(12) United States Patent
Dockal et al.

(10) Patent No.: US 8,546,096 B2
(45) Date of Patent: Oct. 1, 2013

(54) METHOD FOR IDENTIFYING A NON-ANTICOAGULANT SULFATED POLYSACCHARIDE WHICH ENHANCES BLOOD COAGULATION DEPENDENCE ON FXI

(75) Inventors: Michael Dockal, Vienna (AT); Friedrich Scheiflinger, Vienna (AT); Peter Turecek, Klosterneuburg (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 334 days.

(21) Appl. No.: 13/002,501

(22) PCT Filed: Aug. 21, 2009

(86) PCT No.: PCT/EP2009/006082
§ 371 (c)(1),
(2), (4) Date: Jan. 3, 2011

(87) PCT Pub. No.: WO2010/020423
PCT Pub. Date: Feb. 25, 2010

(65) Prior Publication Data
US 2011/0110921 A1 May 12, 2011

Related U.S. Application Data

(60) Provisional application No. 61/189,734, filed on Aug. 22, 2008.

(51) Int. Cl.
*C12Q 1/56* (2006.01)
(52) U.S. Cl.
USPC .......................................................... 435/13
(58) Field of Classification Search
None
See application file for complete search history.

(56) References Cited

U.S. PATENT DOCUMENTS

| | | |
|---|---|---|
| 2003/0203845 A1 | 10/2003 | Knudsen et al. |
| 2005/0282771 A1 | 12/2005 | Johnson |
| 2009/0098185 A1 | 4/2009 | Johnson |

FOREIGN PATENT DOCUMENTS

| | | |
|---|---|---|
| EP | 0251134 | 1/1988 |
| JP | 7215990 | 8/1995 |
| JP | 2003171262 | 6/2003 |
| WO | 9918961 | 4/1999 |
| WO | 2004029095 | 4/2004 |
| WO | 2007127298 | 11/2007 |

OTHER PUBLICATIONS

Bates, et al., "The New Heparins," Coron. Artery Dis. 2(2-3):65-74 (1998).
Bishop, et al., "Recombinant Biologics For Treatment Of Bleeding Disorders," Nat. Rev. Drug Discov. 2.(8):684-94 (2004).
Bourin, et al., "Glycosaminoglycans And The Regulation Of Blood Coagulation," Biochem J. 289(Pt 2):313-30 (1993).
Broze, "The Role Of Tissue Factor Pathway Inhibitor In A Revised Coagulation Cascade," Semin. Haematol. 29(3): 159-69 (1992).
Broze, "The Rediscovery And Isolation OfTFPI," 1. T'hromb. Haemost.I(8): 1671-5 (2003).
Brummel Ziedens, et al., "Factor Viia Replacement Therapy In Factor VII Deficiency," J. T'hromb. Haemost. 6(10): 1735-44 (2Q04).
Carcao, et al., "Prophylactic Factor Replacement In Hemophilia," Blood Rev.II(2): I 01-13 (2004).
Church, et al., "Antithrombin Activity Of Fucoidan. The Interaction OfFucoidan With Heparin Cofactor II, Antithrombin III, And Thrombin," J. Bioi. Chem. 264(6):3618-23 (1989).
Goodman-Gilman, "The Pharmacological Basis of Therapeutics" editors Joel G. Hardman and Lee E. Limbard; published by The McGraw-Hill Companies Inc., (2001) pp. 54-56.
Davie, et al., "The Coagulation Cascade: Initiation, Maintenance, And Regulation," Biochemistry 30(43): 10363-70 (1991).
Erhardtsen, et al., "Blocking OfTissue Factor Pathway Inhibitor (TFPI) Shortens The Bleeding Time In Rabbits With Antibody Induced Haemophilia A," Blood Coagul. Fibrinolysis 2(5):388-94 (1995).
Fryer, et al., "Selective O-Desulfation Produces Nonanticoagulant Heparin That Retains Pharmacological Activity In The Lung," J Pharmacol £xp Ther. m(I):208-19 (1997).
Giedrojc, et al., "Comparative Study On The In Vitro And In Vivo Activities Of Heparinoids Derivative Investigated On The Animal Model," J. Cardiovasc. Pharmacol. 34(3):340-5 (1999).
Granert, et al., "Effects Of Polysaccharide Fucoidin On Cerebrospinal Fluid Interleukin-I And Tumor Necrosis Factor Alpha In Pneumococcal Meningitis In The Rabbit," Irifect. Immun. 67(5):2071-4 (1999).
Hirsh, et al., "New Anticoagulants," Blood W(2):453-63 (2005).
Johnson, et al., "Novel Anticoagulants Based On Inhibition Of The Factor ViiaITissue Factor Pathway," Coron. Artery Dis. 2(2-3):83-7 (1998).
Kleesiek, et al., "The 536C—>T Transition In The Human Tissue Factor Pathway Inhibitor (TFPJ) Gene Is Statistically Associated With A Higher Risk For Venous Thrombosis," Thromb. Haemost. 82(1):1-5 (1999).
Official Action in U.S. Appl. No. 12/316,632, Mail Date Jun. 25, 2009, 11 pages.
Lee, "Von Willebrand Disease, Hemophilia A And B, And Other Factor Deficiencies," Int. Anesthesiol. Clin. 42(3):59-76 (2004).
Liu, et al., "Improved coagulation in bleeding disorders by Non-Anticoagulant Sulfated Polysaccharides (NASP)," Thrombosis and Haemostasis 95:68-76 (2006).

(Continued)

*Primary Examiner* — Sandra Saucier
(74) *Attorney, Agent, or Firm* — Bozicevic, Field & Francis LLP; Bret E. Field; Khin K. Chin

(57) ABSTRACT

A method of identifying a non-anticoagulant sulfated polysaccharide (NASP) which is capable of enhancing blood coagulation in dependence of FXI, the method comprising: a) combining a blood or plasma sample having activation competent FXI with a sulfated polysaccharide and measuring the clotting or thrombin generation parameters of the blood or plasma sample; b) combining a corresponding blood or plasma sample deficient In activation competent FXI with a sulfated polysaccharide and measuring the clotting or thrombin generation parameters of the blood or plasma sample and c) comparing the clotting or thrombin generation parameters of the blood or plasma samples as determined in steps (a) and (b) with each other.

14 Claims, No Drawings

(56) References Cited

OTHER PUBLICATIONS

Luyt, et al., "Low-Molecular-Weight Fucoidan Promotes Therapeutic Revascularization In A Rat Model Of Critical Hindlimb Ischemia," J. Pharmacol. Exp. Ther. 305(1):24-30 (2003).

MacGregor, et al., "Metabolism Of Sodium Pentosan Polysulphate In Man Measured 'By A New Competitive Binding Assay For Sulphated Polysaccharides—Comparison With Effects Upon Anticoagulant Activity, Lipolysis And Platelet Alpha-Granule Proteins," Thromb. Haemost. 53(3):4II-4 (1985).

Mann, "Thrombin: Can't Live Without It; Probably Die From It," Chest 124(3 Suppl):IS-3S (2003).

Mann, "Thrombin Formation," Chest 124(3 Suppl):4S-10S (2003).

McAuliffe, et al. Chem.Indus. Magazine 2:170-4 (1997).

McCaffrey et al. Biochem. Biophys. Res. Commun. 184(2):773-81 (1992).

Millet, et al. "Antithrombotic And Anticoagulant Activities Of A Low Molecular Weight Fucoidan By The Subcutaneous Route;" Thromb. Haemost. 81:391-5 (1999).

Nordfang, et al. "Inhibition Of Extrinsic Pathway Inhibitor Shortens The Coagulation Time Of Normal Plasma And Of Hemophilia Plasma," Thromb. Haemost. 66(4):464-67 (1991).

Novotny, et al. "Purification And Properties Of Heparin-Releasable Lipoprotein-Associated Coagulation Inhibitor," Blood 78(2):394-400 (1991).

Orgueira, et al. "Modular Synthesis Of Heparin Oligosaccharides," Chem. Eur. J. 2(1):140-69 (2003).

Rapaport, et al., "The Tissue Factor Pathway: How It Has Become A 'Prima Ballerina'," Thromb. Haemost 74(1):7-17 (\995).

Roberts, et al., "Current Concepts Of Hemostasis: Implications For Therapy," Anesthesiology 100(3):722-30 (2004).

Sinay, "Sugars Slide Into Heparin Activity," Nature 398(6726):377-S (1999).

Toida ei al. Trends in Glyoeseienee and Glyeoteehnology 15(81):29-46 (2003).

van't Veer C et al., "Regulation of Tissue Factor Initiated Thrombin Generation by the Stoichiometric Inhibitors Tissue Factor PA THWA Y Inhibitor, Antithrombin-III, and Heparin Cofactor-II", Journal of Biological Chemistry, American Society of Biolochemical Biologists, Birmingham, US, 272(7):4367-4377 (1997).

Vicente, et al., "Unbalanced Effects Of 1-23 Dermation Sulfates With Different Sulfation Patterns On Coagulation, Thrombosis And Bleeding," Thromb Haenos 86(5): 121 5-1220 (2001).

Wang, et al., "N-Desulfated Non-Anticoagulant Heparin Inhibits Leukocyte Adhesion And Transmigration In Vitro And Attenuates Acute Peritonitis And Ischemia And Reperfusion Injury In Vivo," Inflamm. Res. 51(9):435-43 (2002).

Welsch, et al., "Effect Of Lipoprotein-Associated Coagulation Inhibitor (LACI) On Thromboplastin~Induced Coagulation Of Normal And Hemophiliac Plasmas," Thromb. Res. 64(2):213-22 (1991).

Westrick, et al., "Deficiency Of Tissue Factor Pathway Inhibitor Promotes Atherosclerosis And Thrombosis In Mice," Circulation 103(25):3044-6 (200 I).

Williams, et al., "Comparative Effects Of Heparin And The Sulfatoid GMI474 On Coagulation parameters In Plasma And Blood From Various Species," Gen. Pharmacol. 30(3):337-41 (1998).

Li et al., "Fucoidan: structure and bioactivity" Molecules (2008) vol. 13, No. 8 pp. 1671-1695 XP002574600.

Prasad et al., "Efficacy and safety of a new-class hemostatic drug candidate, AV513, in dogs with homphilia A" Blood, vol. 111, No. 2 (2008) pp. 672-679 XP002574599.

Li et al, "Toxicological Evaluation of Ducoidian Extracted from *Laiminara japonica* in Wistar Rats" Foo Chem Toxicol 43: 421-426 (2005).

Mourao, "Use of Slfated Fucans as Anticoagulant and Antithombotic Agents: Future Perspectives" Curr Pharma Des 10: 967-981 (2004).

METHOD FOR IDENTIFYING A NON-ANTICOAGULANT SULFATED POLYSACCHARIDE WHICH ENHANCES BLOOD COAGULATION DEPENDENCE ON FXI

FIELD OF THE INVENTION

The invention relates to methods for treating bleeding disorders, particularly congenital coagulation disorders caused by a blood factor deficiency, chronic or acute bleeding disorders, or acquired coagulation disorders.

BACKGROUND OF THE INVENTION

Bleeding disorders, and particularly congenital or acquired deficiencies in coagulation factors, are typically treated by factor replacement. Congenital coagulation disorders include hemophilia, a recessive X-linked disorder involving a deficiency of coagulation factor VIII (hemophilia A) or factor IX (hemophilia B), and von Willebrand's disease, a rare bleeding disorder involving a severe deficiency of von Willebrand factor. Hemophilia C is a milder form of hemophilia caused by a deficiency in factor XI. It is usually asymptomatic, but factor replacement therapy may be required during surgery. Acquired coagulation disorders may arise in individuals without a previous history of bleeding as a result of a disease process. For example, acquired coagulation disorders may be caused by inhibitors or autoimmunity against blood coagulation factors, such as factor VIII, von Willebrand factor, factors IX, V, XI, XII and XIII; or by hemostatic disorders such as caused by liver disease, which may be associated with decreased synthesis of coagulation factors. As many as 20% of patients receiving chronic factor replacement therapy may generate neutralizing antibodies to replacement factors. Protein therapeutics are produced by recombinant technology or are prepared from plasma and can only be administered intravenously, which is inconvenient. Conventional therapy for hemophilia A and factor VIII inhibitor patients is accomplished by therapeutics like recombinant factor VIII or procoagulant bypassing agents, for example FEIBA or recombinant factor VIIa. Although effective, development of inhibitory antibodies which render the therapy ineffective is a common occurrence. FVIIa and FEIBA as therapeutics for the treatment of FVIII inhibitor patients have quite short half lives and so require frequent intravenous administration.

Naito and Fujikawa (1991) *J Biol Chem* 266: 7353-7358 and Gailani and Broze Jr (1993) Blood 82: 813-819 both disclose that negatively charged surfaces such as dextran sulfate, sulfatide or, heparin can facilitate the activation of Factor XI by thrombin or Factor XIa in vitro. However, such materials would not have been considered suitable for therapy of blood coagulation disorders. Typical dextran sulfate and heparin compounds have anticoagulant effects in vivo. Furthermore, these agents would activate contact activation factors (Factor XII, high molecular weight kininogen or prekallikrein) in vivo, which could be dangerous. Localized contact activation on platelets was suggested to be of physiologic relevance (Smith S A and Morrissey J H, Thromb Haemost. 2008 Jul. 26. [Epub ahead of print]). Systemic contact activation might lead to a systemic increase in the level of bradykinin which is generated by the cleavage of HMWK by kallikrein-like enzymes. Unregulated bradykinin release might increase vascular permeability, vascular leakage and possibly edema formation. Such a clinical phenotype is known from the disease hereditary angioedema which is characterised by a functional deficiency in the FXIIa inhibitor C1-Inhibitor.

There is a need for non-protein therapeutics for treating bleeding disorders, which are safe, convenient and effective.

The listing or discussion of a prior-published document in this specification should not be taken as an acknowledgement that the document is part of the state of the art or is common general knowledge.

SUMMARY OF THE INVENTION

A first aspect of the invention provides a method of factor XI-dependent blood coagulation enhancement in a subject in need of enhanced blood coagulation comprising administering a therapeutically effective amount of a composition comprising a non-anticoagulant sulfated polysaccharide (NASP) to the subject, wherein the NASP enhances blood coagulation in a factor XI-dependent manner.

A second aspect of the invention provides a method of factor XI-dependent blood coagulation enhancement in a subject in need of enhanced blood coagulation comprising:
(i) selecting a subject that is not deficient for factor XI; and
(ii) administering a therapeutically effective amount of a composition comprising a non-anticoagulant sulfated polysaccharide (NASP) to the subject, wherein the NASP enhances blood coagulation in a factor XI-dependent manner.

A third aspect of the invention provides a method of identifying a non-anticoagulant sulfated polysaccharide (NASP) which is capable of enhancing blood coagulation in dependence on FXI, the method comprising:
a) combining a blood or plasma sample comprising activation competent FXI with a composition comprising a sulfated polysaccharide and measuring the clotting or thrombin generation parameters of the blood or plasma sample;
b) combining a corresponding blood or plasma sample deficient in activation competent FXI with a composition comprising the sulfated polysaccharide and measuring the clotting or thrombin generation parameters of the blood or plasma sample; and
c) comparing the clotting or thrombin generation parameters of the blood or plasma samples as determined in steps (a) and (b) with each other, wherein a decrease in the clotting time of the blood sample or an increase in peak thrombin or decrease in peak time of the plasma sample comprising activation competent FXI compared to the clotting time of the blood sample or peak thrombin or peak time of the plasma sample deficient in activation competent FXI is indicative of a NASP which is capable of enhancing blood coagulation in dependence on FXI.

DETAILED DESCRIPTION OF PREFERRED EMBODIMENTS OF THE INVENTION

According to a first aspect of the invention, blood coagulation is enhanced in a factor XI-dependent manner.

Coagulation factor XI is a member of the intrinsic (contact activation) pathway. Human factor XI is located on chromosome 4, 187.42-187.45 Mb. The accession number in the Swissprot database is P03951. Although synthesized as a single polypeptide chain, FXI circulates as a homo-dimer. Each chain has a relative molecular mass of approximately 80000 g/mol. Typical plasma concentrations of factor XI are 5 mg/l, corresponding to a plasma concentration (of factor XI dimers) of approximately 30 nM. In its activated form, factor XIa activates factor IX by selectively cleaving arg-ala and arg-val peptide bonds.

Enhancement of blood coagulation by a chemical agent can be determined experimentally using techniques that are known in the art. In vitro tests are preferred. Suitable techniques include rotation thromboelastography with whole blood preparations as described in Example 1, and calibrated automated thrombography with plasma preparations as described in Example 2. Typically, normal blood or plasma may be used in such experiments. By "normal" is meant that the blood is from a person or pooled from several persons not having a coagulation disorder. In rotation thromboelastography, enhancement of blood coagulation can be inferred from a reduction in the clotting time (CT) and/or clot formation time (CFT) in the presence of an agent compared with the same parameter in the absence of the agent in normal blood. The CT or CFT may be reduced by at least 5%, at least 10%, preferably at least 50%. In calibrated automated thrombography, enhancement of blood coagulation can be inferred from a reduction in peak time and/or an increase in peak thrombin in the presence of an agent than in the absence of the agent in normal plasma. Thrombin generation time or peak time is the time interval from the start of thrombin generation, to the time of the thrombin peak maximum. In the assay described in Example 2, the start of thrombin generation is the addition of the fluorogenic substrate-calcium mix to the other components in the assay. Thrombin peak maximum, also referred to as Peak IIa or Peak time is the maximal thrombin concentration generated during the assay. Peak time may be reduced by at least 1 min, at least 2 minutes, preferably at least 5 minutes, more preferably at least 10 minutes. Peak thrombin may be increased by at least 5%, at least 10%, preferably at least 20%, more preferably, at least 50%, 100%, 200% or 300%. The skilled person will appreciate that different concentrations of any given agent may need to be tested in order to identify an effect on blood coagulation in the above assays. Typically, concentrations to test are 0.1-500 µg/mL, and generally from 1 to 50 µg/mL.

The ability of NASPs to promote clotting and reduce bleeding may also be readily determined using other in vitro clotting assays (e.g., dPT and aPTT assays) or in vivo bleeding models (e.g. tail snip, transverse cut, whole blood clotting time, or cuticle bleeding time determination in hemophilic mice or dogs). See, for example, PDR Staff. Physicians' Desk Reference. 2004, Anderson et al. (1976) Thromb. Res. 9:575-580; Nordfang et al. (1991) Thromb. Haemost. 66:464-467; Welsch et al. (1991) Thrombosis Research 64:213-222; Broze et al. (2001) Thromb Haemost 85:747-748; Scallan et al. (2003) Blood. 102:2031-2037; Pijnappels et al. (1986) Thromb. Haemost. 55:70-73; and Giles et al. (1982) Blood 60:727-730.

When an agent that enhances blood coagulation is identified, its dependency on FXI can be determined by techniques such as rotation thromboelastography and calibrated automated thrombography, as described above. The assay is performed in normal blood or plasma and also in blood or plasma lacking activation-competent FXI. When the enhancement of coagulation parameters is greater in the presence than in the absence of activation-competent FXI, the mechanism of action of the agent on coagulation is dependent on FXI. This is so even if there is a FXI-independent component to the activity. By "activation-competent FXI" is meant FXI that is capable of being activated to FXIa. "Activation-competent FXI" may also be referred to as coagulation competent FXI or FXI:c. It may be determined by an aPTT based activity assay, such as the assay described in Ingram G I, Knights S F, Arocha-Piñango C L, Shepperd J P, Pérez-Requejo J L, Mills D K. Simple screening tests for the diagnosis of isolated clotting factor defects. With special reference to 'contact factor' defects. J Clin Pathol. 1975 July; 28(7):524-30. Blood or plasma from a person genetically deficient in FXI, i.e. a person having hemophilia C, lacks activation-competent FXI, or has a lower concentration of activation-competent FXI than blood or plasma from a healthy person. A healthy person has on average 100 IU/dL of FXI:c in their plasma. Severe FXI deficiency is defined as a plasma FXI activity of less than 20 IU/dL, and partial FXI deficiency as 20-70 IU/dL (Gomez and Bolton-Maggs (2008) Hemophilia e-publication ahead of print: doi:10.1111/j.1365-2516.2008.01667.x). Deficiencies in FXI may also arise as a consequence of the development of inhibitors, particularly antibody inhibitors, of FXI (Salomon O et al (2006) Sem Hematology 43, S10-12; Bern M M et al (2005) Haemophilia, 11, 20-25.) Normal blood or plasma, which contains activation-competent FXI, can be made deficient in activation-competent FXI by incubation with an inhibitor of FXI activation. Typically, an antibody is used, such as a polyclonal antibody or plasma containing a polyclonal antibody. A suitable affinity purified polyclonal antibody is "GAFXI-AP" from Enzyme Research Laboratories (South Bend Ind., USA).

According to the first aspect of the invention, the composition is administered to a subject in need of enhanced blood coagulation. A need for enhanced blood coagulation may arise due to any bleeding disorder.

By "subject" is included any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species. The term "patient" refers to a living organism suffering from or prone to a condition that can be prevented or treated by administration of a NASP of the invention, and includes both humans and animals.

At least one therapeutically effective cycle of treatment with a NASP will be administered to a subject. By "therapeutically effective cycle of treatment" is intended a cycle of treatment that when administered, brings about a positive therapeutic response with respect to treatment of an individual for a bleeding disorder. Of particular interest is a cycle of treatment with a NASP that improves hemostasis. A "positive therapeutic response" is one in which the individual undergoing treatment according to the invention exhibits an improvement in one or more symptoms of a bleeding disorder, including such improvements as shortened blood clotting times and reduced bleeding and/or reduced need for factor replacement therapy.

The composition comprising the NASP is typically, although not necessarily, administered orally, via injection (subcutaneously, intravenously or intramuscularly), by infusion, or locally. The pharmaceutical preparation can be in the form of a liquid solution or suspension immediately prior to administration, but may also take another form such as a syrup, cream, ointment, tablet, capsule, powder, gel, matrix, suppository, or the like. Additional modes of administration are also contemplated, such as pulmonary, rectal, transdermal, transmucosal, intrathecal, pericardial, intra-arterial, intracerebral, intraocular, intraperitoneal, and so forth. The respective pharmaceutical compositions comprising NASPs and other agents may be administered using the same or different routes of administration in accordance with any medically acceptable method known in the art.

In a particular embodiment, a composition comprising a NASP is used for localized delivery of a NASP, for example for the treatment of bleeding as a result of a lesion, injury, or surgery. The compositions are also suitable for local treatment. For example, a NASP may be administered by injection at the site of bleeding or in the form of a solid, liquid, or ointment, preferably via an adhesive tape or a wound cover. Suppositories, capsules, in particular gastric-juice-resistant capsules, drops or sprays may also be used. The particular preparation and appropriate method of administration are chosen to target the site of bleeding.

The compositions comprising a NASP may be administered prophylactically, for example before planned surgery. Such prophylactic uses will be of particular value for subjects with known pre-existing blood coagulation disorders. In another embodiment of the invention, the pharmaceutical composition comprising a NASP is in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

In one aspect, NASPs may be used in the methods of the invention for improving hemostasis in treating bleeding disorders, particularly those associated with deficiencies of coagulation factors or for reversing the effects of anticoagulants in a subject. NASPs may be administered to a subject to treat bleeding disorders, including congenital coagulation disorders, acquired coagulation disorders, and hemorrhagic conditions induced by trauma. Examples of bleeding disorders that may be treated with NASPs include, but are not limited to, hemophilia A, hemophilia B, von Willebrand's disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrand's factor, a vitamin K deficiency, a disorder of fibrinogen, including afibrinogenemia, hypofibrinogenemia, and dysfibrinogenemia, an $alpha_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy. In certain embodiments, NASPs are used to treat congenital coagulation disorders including hemophilia A, hemophilia B, and von Willebrand's disease. In other embodiments, NASPs are used to treat acquired coagulation disorders, including deficiencies of factor VIII, von Willebrand factor, factor IX, factor V, factor XI, factor XII and factor XIII, particularly disorders caused by inhibitors or autoimmunity against blood coagulation factors, or haemostatic disorders caused by a disease or condition that results in reduced synthesis of coagulation factors.

The needs of the patient will depend on the particular bleeding disorder being treated. For example, a NASP may be administered to treat a chronic condition (e.g., a congenital or acquired coagulation factor deficiency) in multiple doses over an extended period. Alternatively, a NASP may be administered to treat an acute condition (e.g., bleeding caused by surgery or trauma, or factor inhibitor/autoimmune episodes in subjects receiving coagulation replacement therapy) in single or multiple doses for a relatively short period, for example one to two weeks. In addition, NASP therapy may be used in combination with other hemostatic agents, blood factors, and medications. For example, the subject may be administered a therapeutically effective amount of one or more factors selected from the group consisting of factor XI, factor XII, prekallikrein, high molecular weight kininogen (HMWK), factor V, factor Va, factor VII, factor VIII, factor VIIIa, factor IX, factor X, factor XIII, factor II, factor VIIa, and von Willebrand's factor. Treatment may further comprise administering a procoagulant, such as an activator of the intrinsic coagulation pathway, including factor Xa, factor IXa, factor XIa, factor XIIa, and kallikrein; or an activator of the extrinsic coagulation pathway, including tissue factor, factor VIIa, thrombin, and factor Xa. In addition, transfusion of blood products may be necessary to replace blood loss in subjects experiencing excessive bleeding, and in cases of injury, surgical repair may be appropriate to stop bleeding. Depending on the bleeding disorder, it may not be appropriate to administer prekallikrein, high molecular weight kininogen (HMWK) and/or FXII. Typically, where the NASP is administered in combination with a clotting factor, the dose and/or frequency of administration is reduced compared to the dose and/or frequency that would be appropriate if the clotting factor was to be administered without the NASP. Suitably, the dose of clotting factor is at least 1%, and up to 5, 10, 25, 50, 75% or 100% of the appropriate dose that would be used if the clotting factor were administered without the NASP.

According to the first aspect of the invention, the composition administered to the subject comprises a non-anticoagulant sulfated polysaccharide (NASP). "NASP" as used herein refers to a sulfated polysaccharide that exhibits anticoagulant activity in a dilute prothrombin time (dPT) or activated partial thromboplastin time (aPTT) clotting assay that is no more than one-third, and preferably less than one-tenth, the molar anticoagulant (statistically significant increase in clotting time) activity of unfractionated heparin (MW range 8,000 to 30,000; mean 18,000 Daltons). NASPs may be purified and/or modified from natural sources (e.g. brown algae, tree bark, animal tissue) or may be synthesized de novo and may range in molecular weight from 100 Daltons to 1,000,000 Daltons. NASPs may be used in the methods of the invention for improving hemostasis in treating bleeding disorders, particularly those associated with deficiencies of coagulation factors or for reversing the effects of anticoagulants. NASPs are "non-anticoagulant," in that they do not significantly increase clotting times over the range of concentrations studied. Such compounds can be used in the methods of the present invention provided that any anticoagulant activity that they may exhibit only appears at concentrations significantly above the concentration at which they exhibit procoagulant activity. The ratio of the concentration at which undesired anticoagulant properties occur to the concentration at which desired procoagulant activities occur is referred to as the therapeutic index for the NASP in question. The therapeutic index for NASPs of the present invention may be 5, 10, 30, 100, 300, 1000 or more.

As a class, sulfated polysaccharides are characterized by a plethora of biological activities with often favorable tolerability profiles in animals and humans. These polyanionic molecules are often derived from plant and animal tissues and encompass a broad range of subclasses including heparins, glycosaminoglycans, fucoidans, carrageenans, pentosan polysulfates, and dermatan or dextran sulfates (Toida et al. (2003) Trends in Glycoscience and Glycotechnology 15:29-46). Lower molecular weight, less heterogeneous, and chemically synthesized sulfated polysaccharides have been reported and have reached various stages of drug development (Sinay (1999) Nature 398:377-378; Orgueira et al. (2003) Chemistry 9:140-169; Williams et al. (1998) Gen. Pharmacol. 30:337-341).

Sulfated polysaccharides with potential NASP activity include, but are not limited to, glycosaminoglycans (GAGs), heparin-like molecules including N-acetyl heparin (Sigma-Aldrich, St. Louis, Mo.) and N-desulfated heparin (Sigma-Aldrich), sulfatoids, polysulfated oligosaccharides (Karst et al. (2003) Curr. Med. Chem. 10:1993-2031; Kuszmann et al. (2004) Pharmazie. 59:344-348), chondroitin sulfates (Sigma-Aldrich), dermatan sulfate (Celsus Laboratories Cincinnati, Ohio), fucoidan (Sigma-Aldrich), pentosan polysulfate (PPS) (Ortho-McNeil Pharmaceuticals, Raritan, N.J.), fucopyranon sulfates (Katzman et al. (1973) J. Biol. Chem. 248:50-55), and novel sulfatoids such as GM1474 (Williams et al. (1998) General Pharmacology 30:337) and SR 80258A (Burg et al. (1997) Laboratory Investigation 76:505), and novel heparinoids, and their analogs. NASPs may be purified and/or modified from natural sources (e.g. brown algae, tree bark, animal tissue) or may be synthesized de novo and may range in molecular weight from 100 Daltons to 1,000,000 Daltons. Additional compounds with potential NASP activity include periodate-oxidized heparin (POH) (Neoparin, Inc., San Leandro, Calif.), chemically sulfated laminarin (CSL) (Sigma-Aldrich), chemically sulfated alginic acid (CSAA) (Sigma-Aldrich), chemically sulfated pectin (CSP) (Sigma-Aldrich), dextran sulfate (DXS) (Sigma-Aldrich), heparin-derived oligosaccharides (HDO) (Neoparin, Inc., San Leandro, Calif.).

In principle, any free hydroxyl group on a monosaccharide component of a glycoconjugate can be modified by sulfation to produce a sulfated glycoconjugate for potential use as a NASP in the practice of the invention. For example, such sulfated glycoconjugates may include without limitation sulfated mucopolysaccharides (D-glucosamine and D-glucuronic acid residues), curdlan (carboxymethyl ether, hydrogen sulfate, carboxymethylated curdlan) (Sigma-Aldrich), sulfated schizophyllan (Itoh et al. (1990) Int. J. Immunopharmacol. 12:225-223; Hirata et al. (1994) Pharm. Bull. 17:739-741), sulfated glycosaminoglycans, sulfated polysaccharide-peptidoglycan complex, sulfated alkyl malto-oligosaccharide (Katsuraya et al. (1994) Carbohydr Res. 260:51-61), amylopectin sulfate, N-acetyl-heparin (NAH) (Sigma-Aldrich), N-acetyl-de-O-sulfated-heparin (NA-de-o-SH) (Sigma-Aldrich), de-N-sulfated-heparin (De-NSH) (Sigma-Aldrich), and De-N-sulfated-acetylated-heparin (De-NSAH) (Sigma-Aldrich).

The term "polysaccharide", as used herein, refers to a polymer comprising a plurality (i.e., two or more) of covalently linked saccharide residues. Linkages may be natural or unnatural. Natural linkages include, for example, glycosidic bonds, while unnatural linkages may include, for example, ester, amide, or oxime linking moieties. Polysaccharides may have any of a wide range of average molecular weight (MW) values, but generally are of at least about 100 Daltons. For example, the polysaccharides can have molecular weights of at least about 500, 1000, 2000, 4000, 6000, 8000, 10,000, 20,000, 30,000, 50,000, 100,000, 500,000 Daltons or even higher. Polysaccharides may have straight chain or branched structures. Polysaccharides may include fragments of polysaccharides generated by degradation (e.g., hydrolysis) of larger polysaccharides. Degradation can be achieved by any of a variety of means known to those skilled in the art including treatment of polysaccharides with acid, base, heat, or enzymes to yield degraded polysaccharides. Polysaccharides may be chemically altered and may have modifications, including but not limited to, sulfation, polysulfation, esterification, and methylation.

A NASP may be a derivative or fragment of a polysaccharide.

By "derivative" is intended any suitable modification of the reference molecule of interest or of an analog thereof, such as sulfation, acetylation, glycosylation, phosphorylation, polymer conjugation (such as with polyethylene glycol), or other addition of foreign moieties, so long as the desired biological activity (e.g., clotting activity) of the reference molecule is retained. For example, polysaccharides may be derivatized with one or more organic or inorganic groups. Examples include polysaccharides substituted in at least one hydroxyl group with another moiety (e.g., a sulfate, carboxyl, phosphate, amino, nitrile, halo, silyl, amido, acyl, aliphatic, aromatic, or a saccharide group), or where a ring oxygen has been replaced by sulfur, nitrogen, a methylene group, etc. Polysaccharides may be chemically altered, for example, to improve procoagulant function. Such modifications may include, but are not limited to, sulfation, polysulfation, esterification, and methylation. Methods for making analogs and derivatives are generally available in the art.

By "fragment" is intended a molecule consisting of only a part of the intact full-length sequence and structure. A fragment of a polysaccharide may be generated by degradation (e.g., hydrolysis) of a larger polysaccharide. Active fragments of a polysaccharide will generally include at least about 2-20 saccharide units of the full-length polysaccharide, preferably at least about 5-10 saccharide units of the full-length molecule, or any integer between 2 saccharide units and the full-length molecule, provided that the fragment in question retains biological activity, such as clotting activity.

Preferably, the NASP is not an activator of the contact pathway. By this, we mean it does not contribute to activation of Factor XII. Preferably, the NASP does not activate HMWK or prekallikrein.

Preferably, the NASP is selected from the group consisting of pentosan polysulfate (PPS), fucoidan, N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS) and heparin-derived oligosaccharides (HDO).

More preferably, the NASP is PPS or fucoidan. Fucoidan is a polysaccharide composed largely of sulfated esters of fucose, with a variable degree of branching. Linkages may be predominantly $\alpha(1\rightarrow 2)$ or $\alpha(1\rightarrow 3)$. $\alpha(1\rightarrow 4)$ linkages may also be present. The fucose esters are predominantly sulfated at position 4 and/or 2 and/or 3. Monosulfated fucoses dominate, although desulfated fucose may also be present. In addition to sulfated fucose esters, fucoidan may also contain non-sulfated fucose, D-xylose, D-galactose, uronic acid, glucuronic acid or combinations of more than one of these. F-fucoidan is >95% composed of sulfated esters of fucose, whereas U-fucoidan is approximately 20% glucuronic acid.

Preferably, the NASP enhances the activation of factor XI. In this embodiment, the first aspect of the invention provides a method of enhancing the activation of factor XI in a subject in need of enhanced blood coagulation. By "enhancing the activation of factor XI" we mean that factor XI is activated more quickly and or to a greater extent in the presence than the absence of an effective concentration of the NASP. Without wishing to be bound by theory, NASPs may activate factor XI directly, indirectly, or by a combination of direct and indirect means. Methods such as rotation thromboelastography with whole blood preparations and calibrated automated thrombography with plasma preparations, or other methods as described above which are useful to determined enhancement of blood coagulation, and factor XI-dependency of such enhancement, may be used to identify activation of factor XI. Typically, factor XI-dependent enhancement of blood coagulation is established for the NASP as described above. Then, blood or plasma deficient in activation-competent factor XI is supplemented with activated factor XI. If the NASP fails to enhance blood coagulation in the supplemented blood or plasma, compared to supplemented blood or plasma lacking the NASP, yet exhibits a factor XI-dependent enhancement of blood coagulation, it can be inferred that the NASP acts by enhancing the activation of factor XI. Factor XIa may be used at a concentration of about 20 to 200 pM, suitably 60 pM.

Preferably according to the method of the first aspect, the NASP is administered at a dosage of about 0.005 mg/kg to about 200 mg/kg, typically from about 0.01 mg/kg to about 200 mg/kg. Generally, a therapeutically effective amount will range from about 0.01 mg/kg to 200 mg/kg of a NASP daily, more preferably from about 0.01 mg/kg to 20 mg/kg daily, even more preferably from about 0.02 mg/kg to 2 mg/kg daily. Preferably, such doses are in the range of 0.01-50 mg/kg four times a day (QID), 0.01-10 mg/kg QID, 0.01-2 mg/kg QID, 0.01-0.2 mg/kg QID, 0.01-50 mg/kg three times a day (TID), 0.01-10 mg/kg TID, 0.01-2 mg/kg TID, 0.01-0.2 mg/kg TID, 0.01-100 mg/kg twice daily (BID), 0.01-10 mg/kg BID, 0.01-2 mg/kg BID, or 0.01-0.2 mg/kg BID. The amount of compound administered will depend on the potency of the specific NASP and the magnitude or procoagulant effect desired and the route of administration. The specific dosing schedule will be known by those of ordinary skill in the art or can be determined experimentally using routine methods. Suitable daily or twice daily doses are 0.005 mg/kg to 0.5 mg/kg by intravenous administration, 0.02 to 2 mg/kg by subcutaneous administration, or 1 to 100 mg/kg by per oral administration. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

Suitably, the subject has a bleeding disorder selected from the group consisting of a congenital coagulation disorder caused by a blood factor deficiency, a chronic or acute bleeding disorder, and an acquired coagulation disorder. Typically, the blood factor deficiency is of one or more factors selected from the group consisting of factor V, factor VII, factor VIII, factor IX, factor X, factor XI, factor XII, factor XIII, and von Willebrand factor.

Alternatively, the cause of the need for enhanced blood coagulation is prior administration of an anticoagulant or surgery or other invasive procedure. Where there has been prior administration of an anticoagulant, the method is for reversing the effects of the anticoagulant in the subject.

The method of the first aspect of the invention may further comprise administering an agent selected from the group consisting of a procoagulant, an activator of the intrinsic coagulation pathway, an activator of the extrinsic coagulation pathway, and a second NASP. A NASP (again, preferably provided as part of a pharmaceutical preparation) can be administered alone or in combination with other NASPs or therapeutic agents, such as hemostatic agents, blood factors, or other medications used to treat a particular condition or disease according to a variety of dosing schedules depending on the judgment of the clinician, needs of the patient, and so forth.

A NASP can be administered prior to, concurrent with, or subsequent to other agents. If provided at the same time as other agents, the NASP can be provided in the same or in a different composition. Thus, NASPs and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising a NASP and a dose of a pharmaceutical composition comprising at least one other agent, such as a hemostatic agent or coagulation factor (e.g. FVIII or FIX), which in combination comprise a therapeutically effective dose, according to a particular dosing regimen. Similarly, one or more NASPs and therapeutic agents can be administered in at least one therapeutic dose. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

A "procoagulant" as used herein refers to any factor or reagent capable of initiating or accelerating clot formation. A procoagulant includes any activator of the intrinsic or extrinsic coagulation pathways, such as a clotting factor selected from the group consisting of factor Xa, factor IXa, factor XIa, factor XIIa, kallikrein, tissue factor, factor VIIa, and thrombin. Other reagents that promote clotting include prekallikrein, APTT initiator (i.e., a reagent containing a phospholipid and a contact activator), Russell's viper venom (RVV time), and thromboplastin (for dPT). Contact activators that can be used in the methods of the invention as procoagulant reagents include micronized silica particles, ellagic acid, sulfatides, kaolin or the like known to those of skill in the art. Procoagulants may be from a crude natural extract, a blood or plasma sample, isolated and substantially purified, synthetic, or recombinant. Procoagulants may include naturally occurring clotting factors or fragments, variants, analogs or muteins thereof that retain biological activity (i.e., promote clotting). Optimal concentrations of the procoagulant can be determined by those of skill in the art. Depending on the bleeding disorder, it may not be appropriate to administer contact activators, such as prekallikrein, kallikrein, high molecular weight kininogen (HMWK) and/or FXII.

The terms "variant", "analog" and "mutein" refer to biologically active derivatives of the reference molecule that retain desired activity, such as clotting activity, in the treatment of a bleeding disorder described herein. In general, the terms "variant" and "analog" in reference to a polypeptide (e.g., clotting factor) refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem Biol. (2000) 7:463-473; and Simon et al., Proc. Natl. Acad. Sci. USA (1992) 89:9367-9371 for descriptions of peptoids). Preferably, the analog or mutein has at least the same clotting activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a molecule consisting of only a part of the intact full-length sequence and structure. A fragment of a polypeptide can include a C-terminal deletion, an N-terminal deletion, and/or an internal deletion of the native polypeptide. Active fragments of a particular protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains biological activity, such as clotting activity, as defined herein.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National Biomedical Research Foundation, Washington, D.C., which adapts the local homology algorithm of Smith and Waterman Advances in Appl. Math. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms. The host organism expresses the foreign gene to produce the protein under expression conditions.

Preferably, the activator of the intrinsic coagulation pathway is factor Xa, factor IXa or factor XIa. In certain circumstances it may also be factor XIIa or kallikrein. Preferably, the activator of the extrinsic coagulation pathway is tissue factor, factor VIIa, thrombin, and factor Xa.

The method of the first aspect of the invention may further comprise administering one or more factors selected from the group consisting of factor XI, factor XII, prekallikrein, high molecular weight kininogen (HMWK), factor V, factor Va, factor VII, factor VIII, factor VIIIa, factor IX, factor X, factor XIII, factor II, factor VIIa, and von Willebrand factor.

Factor XI may be provided as fresh frozen plasma (FFP) or as a factor XI concentrate. Suitable factor XI concentrates are Hemoleven® (Laboratoire français du Fractionnement et des Biotechnologies, Les Ulis, France) and factor XI concentrate (Bio Products Laboratory, Elstree, Hertfordshire, United Kingdom). Recombinant Factor XI is also envisaged. FXII, prekallikrein, HMWK or Factor V may be provided as fresh frozen plasma (FFP). Factor VII may be provided as a concentrate, suitably Factor VII concentrate from Baxter BioScience or Bio Products Laboratory. FVIII Immunate® and Advate® FVIII are both recombinant FVIII products available from Baxter BioScience (Vienna, Austria). Bebulin VH® factor IX complex is available from Baxter BioScience (Vienna, Austria). Factor X may be provided as fresh frozen plasma or as a component in a prothrombin complex concentrate. Factor XIII may be provided as fresh frozen plasma, or as a FXIII concentrate, such as Fibrogammin® P (Centeon Pharma GmbH, Marburg, Germany). Factor II may be provided as fresh frozen plasma or as component in a prothrombin complex concentrate. NovoSeven® recombinant activated FVII is available from Novo Nordisk A/S (Denmark). Von Willebrand factor (vWF) is available as Humate-P® (CSL BEHRING, King of Prussia, Pa.). Recombinant vWF can be obtained as in Schlokat, et al. (1995), "Large Scale Production of Recombinant von Willebrand Factor", *Thrombosis and Haemostasis* 78, 1160 or U.S. Pat. No. 6,114,146 (Baxter AG). FEIBA VH Immuno from Baxter BioScience (Vienna, Austria) is a freeze-dried sterile human plasma fraction with Factor VIII inhibitor bypassing activity. In vitro, FEIBA VH Immuno shortens the activated partial thromboplastin time (APTT) of plasma containing Factor VIII inhibitor. It contains Factors II, IX, and X, mainly non-activated, and Factor VII mainly in the activated form. The product contains approximately equal units of Factor VIII inhibitor bypassing activity and Prothrombin Complex Factors. Prothrombin complex concentrates (PCCs) may be used, for example to increase factor X levels. PCC contains factors II, VII, IX, and X and protein C. Infusion of fresh frozen plasma may be used to provide coagulation factors which are deficient in the subject.

As noted above, where a clotting factor is administered with a NASP, the dose of the clotting factor may be reduced compared to the dose that would be suitable in the absence of the NASP. Typically, rFVIII is administered at about 10 to 60 U/kg in hemophilia A patients. When rFVIII is administered in combination with a NASP, a dose of at least 0.1 or 0.6 U/kg, and up to 1, 2, 5, 7.5, 10, 12, 30, 45 or 60 U/kg may be suitable, for example a dose of 0.1 to 0.6, 1 to 6, 2 to 12, 5 to 30, 7.5 to 45, or 10 to 60 U/kg. Typically, FEIBA is administered at about 50-100 U/kg in hemophilia A inhibitor patients. When FEIBA is administered in combination with a NASP, a dose of at least 0.5 or 1 U/kg, and up 2.5, 5, 10, 12.5, 25, 37.5, 50, 75 or 100 U/kg may be suitable, for example a dose of 0.5 to 1, 2.5 to 5, 5 to 10, 12.5 to 25, 25 to 50, 37.5 to 75 or 50 to 100 U/kg. Similarly, rFVIIa is typically administered at about 90 µg/kg in hemophilia A inhibitor patients. When rFVIIa is administered in combination with a NASP, a dose of at least 0.9 µg/kg and up to 4.5, 9, 22.5, 45, 67.5 or 90 µg/kg may be suitable. A typical dose of Factor XI in Factor XI replacement therapy, such as in treatment of hemophilia C, is 30 U/kg or less, and is usually provided in the form of a Factor XI concentrate. When Factor XI is administered in combination with a NASP, a dose of up to 0.3, 1.5, 3, 7.5, 15, 22.5 or 30 U/kg may be suitable.

Preferably, when the method is for reversing the effects of the anticoagulant in the subject, the subject has been treated with an anticoagulant including, but not limited to, heparin, a coumarin derivative, such as warfarin or dicumarol, TFPI, AT III, lupus anticoagulant, nematode anticoagulant peptide (NAPc2), factor VIIa inhibitors, active-site blocked factor VIIa (factor VIIai), active-site blocked FIXa (factor IXai), factor IXa inhibitors, a factor Xa inhibitor, including fondaparinux, idraparinux, DX-9065a, and razaxaban (DPC906), active-site blocked FXa (factor Xai), an inhibitor of factor Va or VIIIa, including activated protein C (APC) and soluble thrombomodulin, a thrombin inhibitor, including hirudin, bivalirudin, argatroban, or ximelagatran. In certain embodiments, the anticoagulant in the subject may be an antibody or antibody fragment that binds a clotting factor, including but not limited to, an antibody or antibody fragment that binds to Factor V, Factor VII, Factor VIII, Factor IX, Factor X, Factor XIII, Factor II, Factor XI, Factor XII, von Willebrand factor, prekallikrein, or high molecular weight kininogen (HMWK). As an alternative to an antibody or antibody fragment, the anticoagulant may be a small drug-like molecule, peptide or aptamer which binds to a coagulation protein and thereby inhibits its activation or its interaction with another coagulation protein or cell surface.

Suitably, in the method of the first aspect of the invention, the subject is deficient in factor XI, and the method further comprises administering factor XI. By "deficient in factor XI" is intended a subject having no more than 70% of the plasma factor XI:c of a healthy vertebrate of the same species as the subject. Where the subject is a human, they may have a partial deficiency, defined as a plasma factor XI:c activity of 20-70 IU/dL, or a severe deficiency, defined as a plasma factor XI:c activity of less than 20 Factor XI deficiency in humans is referred to as hemophilia C. About 20-50% of individuals with partial deficiency have excessive bleeding, but identifying these persons in advance is difficult. Most individuals with severe deficiency do not spontaneously bleed, but they are at risk of bleeding after surgery. The conventional therapy for hemophilia C is administration of fresh frozen plasma, factor XI concentrate or antifibrinolytic agents like tranexamic acid and ε-aminocaproic acid. Factor XI of recombinant origin is also envisaged. Although the coagulation enhancing effect of a NASP according to the present invention is dependent on factor XI, it is believed that the small quantities of factor XI present in subjects having a factor XI deficiency may be sufficient for administration of a NASP to be effective. However, administration of a NASP and factor XI will increase the effectiveness of the NASP in enhancing blood coagulation in factor XI deficient subjects.

Suitably, in the method of the first aspect of the invention, the subject is deficient in factor VIII, and the method further comprises administering factor VIII or a procoagulant bypassing agent. Suitable factor VIII products are FVIII Immunate® and Advate® FVIII (Baxter BioScience, Vienna, Austria). A suitable bypassing agent is FEIBA VH Immuno (Baxter BioScience, Vienna, Austria). The inventors have found that the coagulation enhancing effect of NASPs is additive with the effect of exogenous FVIII in FVIII deficient plasma. Thus NASPs may be used as an adjunct therapy in treatment or prophylaxis of hemophilia A. In this embodiment of the invention, the patient may have inhibitor antibodies against factor VIII. Typically, inhibitor patients are treated with a bypassing agent, such as FEIBA. Such inhibitor patients may have either a high titer response of greater than 5 BU or a low titer response of between 0.5 and 5 BU. For clinical purposes, the magnitude of the antibody response can be quantified through the performance of a functional inhibitor assay from which the Bethesda unit (BU) inhibitor titer can be obtained. The International Society of Thrombosis and Haemostasis (ISTH) definition of a high titer response is >5

BUs and its definition of a low titer response is between 0.5 and 5 BUs. The magnitude of the antibody response to FVIII can be quantified using a functional inhibitor assay, such as that described in Kasper C K et al (1975) Proceedings: A more uniform measurement of factor VIII inhibitors. *Thromb. Diath. Haemorrh.* 34(2):612.

Suitably, in the method of the first aspect of the invention, the subject is deficient in factor IX, and the method further comprises administering factor IX. A suitable factor IX is Bebulin VH® factor IX complex (Baxter BioScience, Vienna, Austria). In this embodiment of the invention, the patient may have inhibitor antibodies against factor IX. FIX inhibitors could be quantified by an aPTT assay as described by Kasper (supra). Suitably, factor 1× and/or FEIBA are also administered to the factor IX deficient subject.

Preferably, according to the method of the first aspect of the invention, a NASP is administered via a non-intravenous route.

A NASP composition for use in the method of the first aspect of the invention may further comprise one or more pharmaceutically acceptable excipients to provide a pharmaceutical composition. Suitable excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

The amount of the NASP (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The NASP compositions herein may optionally include one or more additional agents, such as hemostatic agents, blood factors, or other medications used to treat a subject for a condition or disease. Particularly preferred are compounded preparations including one or more blood factors such as factor XI, factor V, factor VII, factor VIII, factor IX, factor X, factor XIII, factor II, factor VIIa, and von Willebrand factor. Preparations may also include prekallikrein, high molecular weight kininogen (HMWK) and/or factor XII. NASP compositions may also include other procoagulants, such as an activator of the intrinsic coagulation pathway, including but not limited to, factor Xa, factor IXa, factor XIa, factor XIIa, and kallikrein; or an activator of the extrinsic coagulation pathway, including but not limited to, tissue factor, factor VIIa, thrombin, and factor Xa. NASP compositions may include naturally occurring, synthetic, or recombinant clotting factors or fragments, variants or covalently modified derivatives thereof that retain biological activity (i.e., promote clotting). Alternatively, such agents can be contained in a separate composition from the NASP and co-administered concurrently, before, or after the NASP composition of the invention.

A second aspect of the invention provides a method of factor XI-dependent blood coagulation enhancement in a subject in need of enhanced blood coagulation comprising:
  (i) selecting a subject that is not deficient for factor XI; and
  (ii) administering a therapeutically effective amount of a composition comprising a non-anticoagulant sulfated polysaccharide (NASP) to the subject,
wherein the NASP enhances blood coagulation in a factor XI-dependent manner.

Typically, the factor XI status of the subject is determined in order to identify whether they are suitable for treatment according to this aspect of the invention. Deficiency in FXI:c may be determined by an aPTT based activity assay, such as in Ingram G I et al (supra). ELISAs to detect FXI antigen may also be used, and/or genetic analyses to identify a mutation in the FXI gene. If the subject is deficient in factor XI, it may be appropriate to treat them according to the method of the first aspect of the invention, such as by administering factor XI and a NASP. If the subject is not deficient in factor XI, they may suitably be treated according to the method of the second aspect of the invention.

In this aspect of the invention, the NASP enhances blood coagulation in a factor XI-dependent manner. Factor XI-dependent enhancement of blood coagulation may be determined as described in relation to the first aspect of the invention.

As described in the Examples, factor XI-dependent enhancement of blood coagulation by a NASP is more readily detected under conditions in which the tissue factor concentration is low. In a subject, tissue factor concentration is likely to be low at sites which bleed spontaneously, or in response to mild trauma, for example muscles or joints. Hemophilia A or B patients may bleed at these sites. Hemophilia A patients may also be subject to spontaneous bleeding in the brain or digestive tract. As the factor XI-dependent effect of a NASP in enhancing blood coagulation is likely to be important in the treatment of such bleeds, it is preferred to select a subject which is not deficient in factor XI. Preferably, the subject has at least 70 IU/dL and typically about 100 IU/dL of FXI:c in their plasma.

The method of the second aspect of the invention may also be useful where the subject is in need of enhanced blood coagulation for other reasons, for example to reverse the effect of administered anti-coagulants.

According to a third aspect of the invention is provided a method of identifying a non-anticoagulant sulfated polysaccharide (NASP) which is capable of enhancing blood coagulation in dependence on FXI.

In steps (a) and (b), blood or plasma comprising or deficient in activation competent factor XI is combined with a sulfated polysaccharide and the clotting or thrombin generation parameters of the blood or plasma samples are measured. Techniques and blood or plasma preparations as described in relation to the first aspect of the invention are suitable for this purpose.

The blood or plasma sample deficient in activation competent FXI is a "corresponding" sample to the blood or plasma sample comprising activation competent FXI. By "corresponding" is meant that the samples are similar other than with respect to the presence of activation competent FXI. Typically they are from the same species, and preferably have similar levels of other coagulation factors and molecules that influence coagulation. Suitably, the samples are obtained from the same subject, and one is treated to make it deficient in activation competent FXI. Alternatively, the sample deficient in FXI may be obtained from a genetically FXI deficient subject, or pooled material from two or more such subjects. The sample comprising activation competent FXI may be obtained from a normal subject, or pooled material from two or more such subjects.

Step (c) of the method of the third aspect comprises comparing the clotting or thrombin generation parameters of the blood or plasma samples as determined in steps (a) and (b), wherein a decrease in the clotting time of the blood sample or an increase in peak thrombin or decrease in peak time of the plasma sample comprising activation competent FXI compared to the clotting time of the blood sample or peak thrombin or peak time of the plasma sample deficient in activation competent FXI is indicative of a NASP which is capable of enhancing blood coagulation in dependence on FXI.

A NASP identified as being capable of enhancing blood coagulation in dependence on factor XI may be used in a method according to the first or second aspects of the invention.

It is typical to include tissue factor in an assay to measure the clotting or thrombin generation properties of a blood or plasma sample. However, in the method of the third aspect of the invention, it may be necessary to inhibit or reduce clotting or thrombin generation driven by the extrinsic pathway, in order to detect a factor XI-dependent NASP-mediated enhancement of blood coagulation. It has been found that the factor XI-dependent component of NASP-mediated enhancement of blood coagulation in normal human blood or plasma is more readily detected where the tissue factor concentration is low. Suitably, the tissue factor concentration in a plasma assay may be less than 40 pM, less than 20 pM, 5 pM, 1 pM, 0.5 pM, less than 0.2 pM or approximately 0 pM. Suitably, the tissue factor concentration in a blood assay may be less than 1 pM, less than 500 fM, less than 100 fM, less than 50, 20 or 10 fM. It may also be necessary to inhibit or reduce the first step of the intrinsic pathway, that of activation of FXII, in order to identify a factor XI-dependent NASP-mediated enhancement of blood coagulation. Factor XII deficient blood or plasma could be used. Alternatively, an inhibitor of factor XII may be included in the assay, such as corn trypsin inhibitor (CTI). A concentration of 40 µg/mL CTI may be effective. Other features of suitable assays, and components that may be included, are known to the person of ordinary skill in the art, and are also illustrated in the Examples.

The present invention will be further illustrated in the following examples, without any limitation thereto.

Example 1

Fucoidan Improves Clot Formation in Whole Blood

Fucoidan improves clotting parameters in FVIII inhibited blood, and so may be useful in the treatment of hemophilia A.
Materials Blood samples from a healthy individual were drawn into citrated Venoject® tubes (Terumo Europe, Leuven, Belgium (127 mmol/L)) mixing one part of citrate with nine parts of blood by a 21-G butterfly needle. The first tube aspirated was discarded. A proportion of these blood samples were incubated with high titer heat inactivated anti-human FVIII antiserum raised in goat (3876 BU/ml; Baxter BioScience, Vienna, Austria) resulting in 150 BU/mL. Test samples were prepared by dissolving quantities of sulfated polysaccharide in Hepes buffered saline and adding human serum albumin (Sigma-Aldrich Corporation, St. Louis, Mo., USA) to a concentration of 5 mg/mL. A control sample was prepared in which no sulfated polysaccharide was included. The sulfated polysaccharide was *Undaria pinnatifida* fucoidan of ~127 Da (Kraeber GmbH & Co; Ellerbek, Germany).
Method Continuous visco-elastic assessment of human whole blood clot formation and firmness was performed by rotation thromboelastography with whole blood preparations in the presence or absence of sulfated polysaccharides. Briefly, blood is added into a disposable cuvette in a heated cuvette holder. A disposable pin (sensor) is fixed on the tip of a rotating axis. The axis is guided by a high precision ball bearing system and rotates back and forth. The axis is connected with a spring for the measurement of elasticity. The exact position of the axis is detected by the reflection of light on a small mirror on the axis. The loss of elasticity when the sample clots leads to a change in the rotation of the axis. The data obtained are analysed on a computer and visualized in a thromboelastogram. The thromboelastogram shows elasticity (mm) versus time (s). An elasticity of close to zero is observed before clot formation begins. Mirror image traces above and below the zero line indicate the effect of clot formation on the rotation of the axis.

Recordings were made using a ROTEG thromboelastography coagulation analyser (Pentapharm, Munich, Germany) at 37° C. Before starting each experiment, the citrated whole blood was mixed with corn trypsin inhibitor (CTI) (Hematologic Technologies, Inc., Essex Junction, Vt., USA) providing a final concentration of 52 µg/mL for specific inhibition of FXIIa, in order to inhibit FXIIa-mediated contact activation. The analytical set-up was as follows: To 20 µL of test sample or control, 300 µL of pre-warmed (37° C.) CTI treated citrated whole blood was added, followed by 20 µL of a 1:15 dilution of TF PRP reagent containing recombinant human tissue factor (rTF, 3 pM) (TS40, Thrombinoscope By, Maastricht, The Netherlands). Coagulation was initiated by the addition of 20 µL 200 mM $CaCl_2$ (star-TEM®, Pentapharm, Munich, Germany) and recordings were allowed to proceed for at least 120 min. The final concentration of rTF in the assay was 11 fM.

The thromboelastographic parameters of clotting time (CT), clot formation time (CFT) and maximum clot firmness (MCF) were recorded in accordance with the manufacturer's instructions. CT is defined as the time from the start of measurement to the start of clot formation. CFT is defined as the time from the start of clot formation until an amplitude of 20 mm is reached. MCF is the maximum difference in amplitude between the two traces during the assay. The first derivative of the data of the thromboelastogram are plotted to obtain a graph of velocity (mm/s) against time (s). From this graph, the maximum velocity (maxV) is determined. The time at which the maximum velocity is obtained (maxV-t) is also determined.
Results The effect of fucoidan from *Undaria pinnatifida* on thromboelastographic parameters was tested at two concentrations in FVIII-inhibited blood. Two controls were performed in which no fucoidan was present. One used FVIII-inhibited blood and the other used normal blood. Results are shown in Table 1 below. The FVIII-inhibited blood had a characteristically long clotting time and clot formation time. The clotting time and clot formation time were both shorter in the FVIII-inhibited blood containing fucoidan, with the fucoidan exerting a concentration dependent effect on both parameters. Fucoidan also reduced CT and CFT in normal blood.

TABLE 1

| Fucoidan/blood | Clotting parameters | | |
|---|---|---|---|
| | CT (s) | CFT (s) | MCF (mm) |
| Control - FVIII-inhibited blood | 2447 | 881 | 55 |
| U. p. 10 nM - FVIII inhibited blood | 1163 | 419 | 55 |
| U. p. 100 nM - FVIII inhibited blood | 956 | 330 | 50 |
| Control - Normal blood | 869 | 274 | 45 |
| U. p. 10 nM - Normal blood | 767 | 225 | 46 |
| U. p. 100 nM - Normal blood | 382 | 105 | 54 |

Example 2

Calibrated Automated Thrombography (CAT) to Study Thrombin Generation

The procoagulant activity of sulfated polysaccharides was examined in several plasmas from patients with congenital coagulation factor deficiencies, in order to study the mechanism of action. This example describes the basic method which is used in the later examples.

Materials

Plasmas from patients with congenital coagulation factor deficiencies were obtained from George King, Bio-Medical Inc. Kansas USA. According to the supplier, the residual coagulation factor activity for each of the plasmas was lower than 1% except for prothrombin deficient plasma which was 4%. As a model for antibody mediated FVIII deficiency fresh frozen pooled normal plasma (George King, Bio-Medical Inc., Kansas, USA) was incubated with high titer heat inactivated anti-human FVIII plasma raised in goat (4490 BU/ml; Baxter BioScience, Vienna, Austria) giving rise to 50 BU/mL. In some experiments FXI activity of pooled normal plasma or FVIII deficient plasma was blocked by an anti human FXI antibody (GAFXI-AP, Enzyme Research Laboratories, South Bend, Ill., USA) at a final concentration of 100 nM. If not indicated otherwise, the plasmas were mixed with corn trypsin inhibitor (CTI) (Hematologic Technologies, Inc., Essex Junction, Vt., USA), providing a final concentration of 40 µg/mL, for specific inhibition of factor XIIa.

Test samples were prepared by dissolving quantities of sulfated polysaccharide in Hepes buffered saline and adding human serum albumin (Sigma-Aldrich Corporation, St. Louis, Mo., USA) to a concentration of 5 mg/mL. The sulfated polysaccharides and their sources are indicated in Table 2 below.

TABLE 2

| Sulfated polysaccharide | MW (kDa) | Source |
|---|---|---|
| Pentosan polysulfate sodium (PPS) | 5.9 | CF Pharma Ltd. (Budapest, Hungary) |
| Fucoidan LMW, Ascophyllum nodosum | 7.5 | Kraeber GmbH & Co (Ellerbek, Germany) |
| Fucoidan, Fucus vesiculosus | ~115.5 | F6531; Sigma-Aldrich Chemie GmbH (Taufkirchen, Germany) |
| Fucoidan, Undaria pinnatifida | ~127 | Kraeber GmbH & Co (Ellerbek, Germany) |
| Fucoidan HMW, Ascophyllum nodosum | ~600 | Kraeber GmbH & Co (Ellerbek, Germany) |
| Fucoidan, Laminaria japonica | >1000 | Kraeber GmbH & Co (Ellerbek, Germany) |

Reference samples were prepared from reference proteins FVIII Immunate® reference standard (Baxter BioScience, Vienna, Austria); Factor eight inhibitor by-passing activity (FEIBA) reference standard (Baxter BioScience, Vienna, Austria); NovoSeven® recombinant activated FVII (Novo Nordisk A/S, Denmark) and purified human plasma FIX (Enzyme Research Laboratories, South Bend, Ill., USA). A proprietary thrombin calibrator compound was obtained from Thrombinoscope BV, Maastricht, The Netherlands.

Method

The influence of each sulfated polysaccharide on thrombin generation was measured in duplicate via calibrated automated thrombography in a Fluoroskan Ascent® reader (Thermo Labsystems, Helsinki, Finland; filters 390 nm excitation and 460 nm emission) following the slow cleavage of the fluorogenic substrate Z-Gly-Gly-Arg-AMC (Hemker H C. Pathophysiol Haemost Thromb 2003; 33: 4 15). To each well of a 96 well micro-plate (Immulon 2HB, clear U-bottom; Thermo Electron) 80 µL of pre-warmed (37° C.) plasma was added. For triggering thrombin generation by tissue factor, 10 µL of PPP reagent containing a certain amount of recombinant human tissue factor (rTF) and phospholipid vesicles composed of phosphatidylserine, phosphatidylcholine and phosphatidylethanolamine (48 µM) (Thrombinoscope BV, Maastricht, The Netherlands) was added. Alternatively, a mix of rTF (Innovin®, Siemens Healthcare Diagnostics Inc., Tarrytown, N.Y., USA) and a phospholipid emulsion composed of phosphatidylcholine, phosphatidylserine and sphingomyelin (Phospholipid-TGT, Rossix, Mölndal, Sweden) was used. If thrombin generation was triggered by factor XIa, a mix of human factor XIa (0.72 nM) (Enzyme research Laboratories, South Bend, Ind., USA) and Phospholipid-TGT (48 µM) was added. If thrombin generation without the addition of any trigger was studied, just 10 µL Phospholipid-TGT (48 µM) diluted in Hepes buffered saline was included. Just prior to putting the plate into the pre-warmed (37° C.) reader, 10 µL of test or reference sample or calibrator compound was added. Thrombin generation was started by dispensing 20 µL of FluCa reagent (Thrombinoscope BV, Maastricht, The Netherlands) containing fluorogenic substrate and Hepes buffered $CaCl_2$ (100 mM) into each well and fluorescence intensity was recorded at 37° C.

The parameters of the resulting thrombin generation curves were calculated using the Thrombinoscope™ software (Thrombinoscope BV, Maastricht, The Netherlands) and thrombin calibrator to correct for inner filter and substrate consumption effects (Hemker H C. *Pathophysiol Haemost Thromb* 2003; 33: 4 15). With the thrombin calibrator as a reference, the molar concentration of thrombin in the test wells was calculated by the software. The thrombin amounts at the peak of each thrombin generation curve (peak thrombin, nM) were plotted against the peak thrombin obtained from standard concentrations of a reference protein (FVIII Immunate® reference standard, FEIBA reference standard) and fitted by a non-linear algorithm. Based on this calibration, FVIII Immunate®, FEIBA and FIX equivalent activities were calculated. Other parameters recorded were lag time (time interval between starting measurement and start of thrombin generation), peak time (time interval between starting measurement and peak thrombin) and endogenous thrombin potential (area under curve of thrombin concentration versus time).

Example 3

Tissue Factor and FVIII Dependency of Thrombin Generation

Tissue factor and FVIII dependency of thrombin generation were assessed using the CAT assay. Pooled normal plasma and FVIII inhibited plasma were tested in the presence of tissue factor at 1, 5 or 20 pM. As expected, at each concentration of tissue factor, the peak thrombin was reduced in the FVIII inhibited plasma compared to normal plasma, and the peak time was increased. The most pronounced difference between the thrombin generation parameters of the two plasmas was observed at the lowest tissue factor concentration. Results are shown in Table 3 below.

TABLE 3

| Tissue factor (pM) | Plasma | | Ratio Normal/ FVIII inhibited |
|---|---|---|---|
| | Normal | FVIII inhibited | |
| | Peak thrombin (nM) | | |
| 1 | 94.4 | 29.9 | 3.16 |
| 5 | 276.5 | 173.3 | 1.60 |
| 20 | 398.1 | 346.5 | 1.15 |
| | Peak time (min) | | |
| 1 | 11.89 | 17.92 | 0.66 |
| 5 | 5.24 | 6.15 | 0.85 |
| 20 | 3.43 | 3.48 | 0.99 |

As the deficiency of thrombin generation in FVIII deficient plasma was most pronounced at low tissue factor concentrations as indicated by the highest ratio (normal:FVIII inhibited) of Peak thrombin, and lowest ratio (normal:FVIII inhibited) of Peak time, later experiments designed to identify the effect of sulfated polysaccharides on thrombin generation were generally performed at a low tissue factor concentration.

Example 4

Hemophilia Therapeutics Improve Thrombin Generation in FVIII Inhibited or Deficient Plasma To provide a reference with which to compare the efficacy of sulfated polysaccharides, hemophilia therapeutics were tested in the CAT assay at a range of concentrations in FVIII inhibited or hemophiliac plasma. A control using normal plasma was run for comparison. FVIII Immunate® was tested at 0, 25, 100, 250, 500 and 1000 mU/ml in hemophilia A plasma. FEIBA was tested at 0, 10, 40, 100, 250 and 500 mU/ml in FVIII inhibited plasma. rFVIIa Novoseven® was tested at 0, 0.04, 0.2, 1, 5 and 25 nM. For each hemophilia therapeutic, peak thrombin increased and peak time decreased at increasing concentrations of therapeutic agent. The highest concentrations of FVIII Immunate® and FEIBA tested gave rise to thrombin generation parameters that were comparable to that of normal plasma. At the highest concentration of rFVIIa Novoseven® tested, peak time was comparable to that of normal plasma, and peak thrombin was about 60% of the level obtained with normal plasma.

Example 5

Sulfated Polysaccharides are Most Effective at Improving Thrombin Generation at Intermediate Concentrations Sulfated polysaccharides were tested at a range of concentrations in hemophilia A plasma. The concentration of tissue factor was 1 pM. At concentrations of up to 100 nM, fucoidan from *Fucus vesiculosus* improved thrombin generation parameters (i.e. increased peak thrombin and decreased peak time) in a concentration-dependent manner. At higher fucoidan concentrations of 250, 500, 1000, 1500 and 2000 nM, thrombin generation parameters deteriorated in a concentration-dependent manner. A similar pattern was observed for each of the sulfated polysaccharides tested, with an optimal effect on thrombin generation at an intermediate concentration, and sub-optimal effects at lower and higher concentrations. The optimal effect was achieved at a comparable µg/ml concentration of each sulfated polysaccharide, although the nM concentrations varied over two orders of magnitude. The FVIII equivalent activity of the concentration of each of the six sulfated polysaccharides tested that had the most beneficial effect on peak thrombin was estimated. Results are shown in Table 4 below.

TABLE 4

| Sulfated polysaccharide | Conc (nM) | Conc (µg/ml) | FVIII EA (mU/ml) |
|---|---|---|---|
| PPS | 1000 | 5.9 | 733 |
| Fuc An LMW | 1000 | 7.5 | 937 |
| Fuc Fv | 100 | 11.6 | 874 |
| Fuc Up | 100 | 12.7 | 869 |
| Fuc An HMW | 25 | 15.0 | 794 |
| Fuc Lj | 10 | 10.0 | 826 |

Further data are given in Table 5 below, indicating the "therapeutic window" for each sulfated polysaccharide. The "therapeutic window" is the concentration range at which the sulfated polysaccharide provides for a peak thrombin in severe hemophilia A plasma (FVIII activity below 1% of normal plasma) which is at least the peak thrombin provided by the addition of 10 mU/mL (1% of normal) of factor VIII (Immunate®) to severe hemophilia A plasma. Also shown is the FVIII equivalent activity of the optimal concentration of sulfated polysaccharide and, in brackets, the FVIII equivalent activity of the polysaccharide concentration at either end of the therapeutic window. The results indicate that each sulfated polysaccharide has a procoagulant effect across a broad concentration range.

TABLE 5

| Sulfated polysaccharide | MW (kD) | Therapeutic window | | |
|---|---|---|---|---|
| | | nM | µg/mL | FVIII EA |
| PPS | 5.9 | 50-20000* | 0.3-118* | 733 (10-46) |
| A. n. LMW | 7.5 | 25-20000* | 0.2-150* | 937 (16-577) |
| F. v. | 115 | 5-2000* | 0.6-230* | 874 (17-334) |
| U. p. | 127 | 5-2000* | 0.6-254* | 869 (28-101) |
| A. n. HMW | 600 | 2.5-500 | 1.5-300 | 794 (67-129) |
| L. j. | >1000 | 1-250 | 1-250 | 826 (42-170) |

*indicates that the upper limit given for the therapeutic window was the highest concentration of sulfated polysaccharide tested.

Similar experiments were performed with the sulfated polysaccharides in FVIII inhibited plasma. In each case, FEIBA equivalent activities were estimated rather than FVIII equivalent activities. Results are presented in the following two tables, and are broadly consistent with the results obtained using hemophilia A plasma.

TABLE 6

| Sulfated polysaccharide | Conc (nM) | Conc (µg/ml) | FEIBA EA (mU/ml) |
|---|---|---|---|
| PPS | 1000 | 5.9 | 587 |
| Fuc An LMW | 1000 | 7.5 | 773 |
| Fuc Fv | 100 | 11.6 | 625 |
| Fuc Up | 100 | 12.7 | 1047 |
| Fuc An HMW | 25 | 15.0 | 1226 |
| Fuc Lj | 10 | 10.0 | 1090 |

TABLE 7

| Sulfated polysaccharide | MW (kD) | Therapeutic window nM | Therapeutic window µg/mL | FEIBA EA mU/mL |
|---|---|---|---|---|
| PPS | 5.9 | 50-10000 | 0.3-59 | 587 (25-189) |
| A. n. LMW | 7.5 | 50-20000* | 0.4-150 | 773 (18-386) |
| F. v. | 115 | 10-2000* | 1.2-230 | 625 (23-230) |
| U. p. | 127 | 10-2000* | 1.3-254 | 1047 (65-85) |
| A. n. HMW | 600 | 2.5-500 | 1.5-300 | 1226 (54-150) |
| L. j. | >1000 | 2.5-250 | 2.5-250 | 1090 (288-175) |

*indicates that the upper limit given for the therapeutic window was the highest concentration of sulfated polysaccharide tested.

A comparison of the FEIBA equivalent activity in FVIII inhibited plasma and the FVIII equivalent activity in hemophilia A plasma for the optimum concentration of each sulfated polysaccharide is shown in Table 8 below.

TABLE 8

| Sulfated polysaccharide | Optimum Concentration (nM) | Optimum Concentration (µg/ml) | FEIBA EA (mU/ml) | FVIII EA (mU/ml) |
|---|---|---|---|---|
| PPS | 1000 | 5.9 | 587 | 733 |
| A. n. LMW | 1000 | 7.5 | 773 | 937 |
| F. v. | 100 | 11.6 | 625 | 874 |
| U. p. | 100 | 12.7 | 1047 | 869 |
| A. n. HMW | 25 | 15.0 | 1226 | 794 |
| L. j. | 10 | 10.0 | 1090 | 826 |

Example 6

Sulfated Polysaccharides Act Additively with Hemophilia Therapeutics in Promoting Thrombin Generation Experiments were performed to examine the effect of fucoidan on peak thrombin in hemophilia A or FVIII inhibited plasma in the presence of increasing concentrations of hemophilia therapeutics. The CAT assay was used to determine peak thrombin with a tissue factor concentration of 1 pM.

A range of concentrations of FVIII Immunate® were tested in hemophilia A plasma, namely 0, 0.1, 1, 10, 100 and 1000 mU/mL. For each concentration, fucoidan from *Undaria pinnatifida* was added at a concentration of 100 nM and a corresponding control was performed in the absence of fucoidan. The ratio of peak thrombin in the presence and absence of fucoidan was calculated for each concentration of Immunate®. Similar experiments were performed using FEIBA at 0, 10, 40, 100, 250 or 500 mU/mL as the hemophilia therapeutic and FVIII inhibited plasma, and using rFVIIa NovoSeven® at 0, 0.04, 0.2, 1, 5 and 25 nM as the hemophilia therapeutic and FVIII inhibited plasma. Results are shown in Table 9 below.

TABLE 9

| Therapeutic/ plasma | Parameter measured | Concentration of therapeutic | | | | | |
|---|---|---|---|---|---|---|---|
| | | 0 | 0.1 | 1 | 10 | 100 | 1000 |
| FVIII mU/ml/ Hem A plasma | Peak thrombin (+fucoidan) | 102.04 | 105.85 | 105.59 | 110.07 | 134.86 | 208.25 |
| | Peak thrombin (−fucoidan) | 36.75 | 36.14 | 36.37 | 38.23 | 50.56 | 102.31 |
| | Ratio | 2.8 | 2.9 | 2.9 | 2.9 | 2.7 | 2.0 |
| | | 0 | 10 | 40 | 100 | 250 | 500 |
| FEIBA mU/ml/ FVIII inhibited | Peak thrombin (+fucoidan) | 120.77 | 124.47 | 130.16 | 152.29 | 198.27 | 258.35 |
| | Peak thrombin (−fucoidan) | 27.58 | 30.27 | 36.96 | 47.04 | 72.12 | 102.71 |
| | Ratio | 4.4 | 4.1 | 3.5 | 3.2 | 2.7 | 2.5 |
| | | 0 | 0.04 | 0.2 | 1 | 5 | 25 |
| rFVIIa nM/ FVIII inhibited | Peak thrombin (+fucoidan) | 119.59 | 127.08 | 145.22 | 179.39 | 208.54 | 212.37 |
| | Peak thrombin (−fucoidan) | 28.05 | 34.43 | 43.63 | 53.87 | 62.04 | 65.19 |
| | Ratio | 4.3 | 3.7 | 3.3 | 3.3 | 3.4 | 3.3 |

The results show that increasing the quantity of hemophilia therapeutic results in an increase in peak thrombin. The enhancement of peak thrombin caused by the addition of fucoidan was slightly greater at lower than higher quantities of FVIII or FEIBA tested, and roughly comparable at all quantities of rFVIIa tested. Thus, fucoidan appears to act additively with hemophilia therapeutics, particularly when the concentration of hemophilia therapeutic is not high enough to promote a physiological amount of thrombin generation. (In this assay, normal plasma produces a peak thrombin of about 100 nM.) Thus, fucoidan may be useful as an adjunct therapy in hemophilia treatment.

Example 7

Tissue Factor Dependency of the Fucoidan Effect

Tissue factor dependency of the effect of fucoidan on thrombin generation parameters was tested by the CAT assay. Peak time and peak thrombin were determined for four different plasma and fucoidan combinations at 0, 0.2, 0.5, 1, 5 and 20 pM tissue factor. The plasmas were pooled normal plasma and FVIII inhibited plasma. Each was tested in the presence or absence of 100 nM fucoidan from *Undaria pinnatifida*. Results are shown in Table 10 below.

TABLE 10

| Plasma | Fucoidan (100 nM) | Parameter | Tissue factor (pM) | | | | | |
|---|---|---|---|---|---|---|---|---|
| | | | 0 | 0.2 | 0.5 | 1.0 | 5.0 | 20.0 |
| Normal | − | Peak time (min) | 44.43 | 24.20 | 19.02 | 15.84 | 9.15 | 4.31 |
| | | Peak thrombin (nM) | 22.67 | 53.36 | 71.91 | 86.60 | 186.1 | 301.2 |
| Normal | + | Peak time (min) | 15.84 | 13.84 | 12.16 | 10.66 | 6.31 | 3.97 |
| | | Peak thrombin (nM) | 291.7 | 199.2 | 198.0 | 208.7 | 263.8 | 309.8 |
| FVIII inhibited | − | Peak time (min) | 120.0 | 53.67 | 43.67 | 35.67 | 15.17 | 5.33 |
| | | Peak thrombin (nM) | 0.26 | 0.73 | 4.47 | 9.48 | 65.32 | 206.6 |
| FVIII inhibited | + | Peak time (min) | 55.00 | 33.67 | 28.83 | 24.33 | 9.83 | 4.67 |
| | | Peak thrombin (nM) | 1.50 | 12.26 | 31.71 | 51.28 | 134.0 | 259.7 |

The results show that the effect of fucoidan in reducing peak time and increasing peak thrombin in normal plasma is most pronounced at the lowest concentrations of tissue factor and particularly when no tissue factor is added. When the concentration of tissue factor is high, thrombin is generated almost exclusively through the extrinsic pathway. Under those conditions, sulfated polysaccharides do not increase thrombin generation. In FVIII inhibited plasma, there is also a trend for fucoidan to have a more pronounced effect on peak time and peak thrombin at low tissue factor concentrations. However, to achieve a physiologically relevant thrombin generation in this assay, some tissue factor is required. Any effect of fucoidan in the total absence of tissue factor may not be meaningful. Even at the highest concentration of tissue factor tested, fucoidan still increased peak thrombin.

As indicated above, fucoidan from *Undaria pinnatifida* is capable of stimulating thrombin generation at low concentrations of tissue factor and even in the absence of tissue factor (in normal plasma). Other sulfated polysaccharides were tested for their effect on thrombin generation in the absence of tissue factor in the CAT assay. Each compound was tested at the optimal concentration as determined in Example 5, with the exception of A.n. HMW which was tested at 10 nM. (Peak thrombin is only slightly lower where A.n. HMW is used as 10 nM, compared to 25 nM.) Results are shown in Table 11 below.

TABLE 11

| | Peak thrombin (nM) | | Peak time (min) | |
|---|---|---|---|---|
| Compound | Normal plasma | FVIII inhibited | Normal plasma | FVIII inhibited |
| Control | 22.67 | 0.26 | 44.43 | >120.00 |
| PPS | 26.22 | 0.24 | 31.56 | 68.33 |
| A. n. LMW | 53.25 | 0.30 | 26.04 | 52.83 |
| F. v. | 46.15 | 0.22 | 28.72 | 58.83 |
| U. p. | 291.74 | 1.50 | 15.84 | 55.00 |
| A. n. HMW | 120.56 | 0.20 | 21.02 | 69.83 |
| Fuc Lj | 61.10 | 0.37 | 26.88 | 75.33 |

The results show that each of the compounds tested are capable of increasing Peak thrombin and reducing Peak time in normal plasma. In the total absence of tissue factor, the compounds did not enhance Peak thrombin or reduce Peak time in FVIII inhibited plasma. This can be explained by the fact that the extrinsic pathway is inactive in the absence of tissue factor, and the intrinsic pathway is inactive in the absence of FVIII.

Example 8

Fucoidan Acts Independently of FXII to Promote Thrombin Generation

Thrombin generation parameters were tested in FXII deficient plasma in the presence or absence of 100 nM fucoidan from *Undaria pinnatifida*, at a tissue factor concentration of 1 pM. Under these conditions, residual FXII activity was lower than 1% of normal, but corn trypsin inhibitor was still included at 40 μg/mL as a precaution. Fucoidan was found to increase peak thrombin and decrease peak time, as in previous experiments. FXII is the starting point of the intrinsic (contact activation) pathway. The fact that fucoidan improves thrombin generation parameters in FXII deficient plasma indicates that it does not act on FXII.

Example 9

Coagulation Factor Dependency of the Effect of Sulfated Polysaccharides

To examine the mechanism of action of sulfated polysaccharides further, CAT assays were performed in further coagulation factor deficient plasmas. No tissue factor was added in order to minimise the contribution of the extrinsic pathway to thrombin generation. The following fucoidans were tested: *Ascophyllum nodosum*, high MW, 10 nM; *Fucus vesiculosus*, 100 nM; *Undaria pinnatifida*, 100 nM; *Ascophyllum nodosum*, low MW, 1000 nM.

When prothrombin deficient plasma was tested, there was essentially no peak thrombin in the control lacking fucoidan. In the presence of each of the fucoidans, there were small peaks, which may be explained by the fact that the prothrombin deficient plasma retained about 4% of the prothrombin activity of normal plasma. When FX deficient plasma was used, no thrombin peaks were observed in the absence or presence of any of the fucoidans. This shows that FX, which is essential for both intrinsic and extrinsic pathways, as it is part of the common pathway, is required for sulfated polysaccharides to promote thrombin generation. Similarly, in FV deficient plasma, no thrombin peaks were observed. FV is part of the prothrombin activating complex of the common pathway, and is necessary for sulfated polysaccharides to promote thrombin generation. In FVII deficient plasma, all fucoidans were capable of generating a thrombin peak, but there was no peak in the absence of fucoidan. FVII is the starting point of the extrinsic pathway, and is not necessary for sulfated polysaccharides to promote thrombin generation. In FIX deficient plasma, a small thrombin peak was observed in the presence of *Undaria pinnatifida* fucoidan, but not in the other samples. FIX is activated in the intrinsic pathway, and appears to be necessary for sulfated polysaccharides to promote substantial thrombin generation. In FVIII deficient plasma, a very small thrombin peak was observed in the presence of *Undaria pinnatifida* fucoidan, but not in the other samples. FVIII is activated in the intrinsic pathway, and appears to be necessary for sulfated polysaccharides to promote substantial thrombin generation. In FXI deficient plasma, no thrombin peaks were observed in the presence or absence of NASPs. FXI is activated in the intrinsic pathway, and appears to be necessary for sulfated polysaccharides to promote thrombin generation. In FXII deficient plasma, a small thrombin peak was observed in the absence of fucoidan. Each of the fucoidans caused a substantial increase in peak thrombin and a reduction in peak time. Thus FXII, which is required for the intrinsic pathway, is not necessary for sulfated polysaccharides to promote thrombin generation. Results are summarised in Table 12 below.

TABLE 12

| Coagulation factor | Role | Necessary for mechanism of sulfated polysaccharides? |
|---|---|---|
| prothrombin | common pathway | yes |
| FX | common pathway | yes |
| FV | common pathway | yes |
| FVII | extrinsic pathway | no |
| FIX | intrinsic pathway | yes |
| FVIII | intrinsic pathway | yes |
| FXI | intrinsic pathway | yes |
| FXII | intrinsic pathway | no |

The coagulation factors of the intrinsic pathway are necessary for sulfated polysaccharide enhancement of thrombin generation, with the exception of FXII, the first coagulation factor of that pathway. The order in which the coagulation factors act in the intrinsic pathway is FXII, followed by FXI, then FIX and FVIII in combination. Finally FX and FV act in combination in the common pathway. The first coagulation factor of this pathway that is required for the sulfated polysaccharides to enhance thrombin generation is FXI. The data therefore suggest that sulfated polysaccharides act on the intrinsic pathway by enhancing the activation of FXI.

The fact that sulfated polysaccharides enhance thrombin generation in the absence of FVII and tissue factor implies that their mechanism of action is independent of the extrinsic pathway and is fully driven through the intrinsic pathway.

Example 10

A FXI-Dependent Mechanism of Fucoidan Activity Contributes to Thrombin Generation when Tissue Factor Concentration is Low The FXI dependency of the effect of sulfated polysaccharides was studied in pooled normal plasma and FXI deficient plasma by CAT assay at different concentrations of tissue factor. The sulfated polysaccharide tested was the *Undaria pinnatifida* fucoidan at 100 nM. As observed in previous experiments, the stimulatory effect of the fucoidan was greater at lower concentrations of tissue factor in normal plasma. As in the previous experiment, fucoidan did not have a stimulatory effect in FXI deficient plasma in the absence of added tissue factor. However, a stimulatory effect was observed at 1, 5 and 20 pM tissue factor in FXI deficient plasma. Results are shown in Table 13 below.

TABLE 13

| Plasma/ fucoidan | Peak thrombin (nM) Tissue factor (pM) | | | | | |
|---|---|---|---|---|---|---|
| | 0 | 0.2 | 0.5 | 1 | 5 | 20 |
| Normal plasma −fucoidan | 22.67 | 53.36 | 71.91 | 86.60 | 186.06 | 301.24 |
| Normal plasma +fucoidan | 291.74 | 199.20 | 198.00 | 208.74 | 263.81 | 309.80 |
| FXI deficient plasma −fucoidan | 0.00 | Not tested | Not tested | 37.24 | 172.17 | 358.87 |
| FXI deficient plasma +fucoidan | 2.41 | Not tested | Not tested | 102.73 | 279.60 | 392.51 |

At increasing concentrations of tissue factor, the contribution of the extrinsic pathway to thrombin generation increases. The stimulatory effect of fucoidan in the presence of tissue factor in FXI deficient plasma may be mediated by the extrinsic pathway. By comparing the stimulatory effect of fucoidan at 0 or 1 pM tissue factor between normal plasma and FXI deficient plasma, it can be seen that at these low tissue factor concentrations, fucoidan has a greater stimulatory effect in normal than FXI deficient plasma. It follows that a FXI dependent mechanism of fucoidan activity contributes to thrombin generation when tissue factor concentration is low.

A further experiment was conducted but instead of using FXI deficient plasma, FXI was inhibited in pooled normal plasma by pre-incubation with anti-FXI antibody. The antibody was polyclonal goat anti-human FXI affinity purified "GAFXI-AP" from Enzyme Research Laboratories (South Bend, Ill., USA). It was used at a concentration of 150 nM to fully inhibit FXI. As a control, the same pooled normal plasma was used untreated. Otherwise, the experiment was performed in the same way as the preceding experiment. Results are shown in Table 14 below.

TABLE 14

| Plasma/ | Peak thrombin (nM) Tissue factor (pM) | | | | | |
|---|---|---|---|---|---|---|
| fucoidan | 0 | 0.2 | 0.5 | 1 | 5 | 20 |
| Normal plasma −fucoidan | 13.56 | 30.22 | 39.28 | 57.77 | 150.39 | 301.64 |
| Normal plasma +fucoidan | 287.07 | 187.86 | 191.16 | 199.59 | 254.10 | 303.78 |
| FXI-inhibited plasma −fucoidan | 0.56 | 5.89 | 16.16 | 33.17 | 133.06 | 303.02 |
| FXI-inhibited plasma +fucoidan | 6.15 | 27.06 | 57.80 | 99.53 | 241.15 | 310.10 |

The results confirm the conclusion that at low tissue factor concentrations, fucoidan stimulates thrombin generation by a FXI-dependent mechanism.

Example 11

Fucoidans Stimulate Thrombin Generation in FXI Deficient Plasma Supplemented with FXI An experiment was performed to examine the effect of supplementing FXI deficient plasma with exogenous FXI. Sulfated polysaccharide-stimulated thrombin generation was measured by CAT assay. No tissue factor was used in this experiment. The sulfated polysaccharide tested was the *Undaria pinnatifida* fucoidan at 100 nM. FXI deficient patient plasma was obtained form George King (Bio-Medical Inc., Kansas, US). It was supplemented with purified human factor XI (Enzyme Research Laboratories, South Bend, Ind., USA) to a concentration of 0, 0.3, 3 or 30 nM exogenous factor XI. 30 nM factor XI is the concentration found in normal human plasma. Thrombin peak time and peak thrombin were tested in the presence or absence of fucoidan. Results are shown in Table 15 below.

TABLE 15

| Compound | Parameter | Factor XI (nM) | | | |
|---|---|---|---|---|---|
| | | 0 | 0.3 | 3 | 30 |
| +fucoidan | Peak time (min) | 38.8 | 38.8 | 28.0 | 21.8 |
| | Peak thrombin (nM) | 2.8 | 14.3 | 56.9 | 134.8 |
| −fucoidan | Peak time (min) | >120 | >120 | >120 | 53.7 |
| | Peak thrombin (nM) | 0.2 | 0.2 | 0.3 | 25.2 |

Results show that fucoidan stimulates thrombin generation in a manner that is dependent on Factor XI concentration.

A further experiment was performed comparing the effects of four different sulfated polysaccharides on thrombin generation in the presence or absence of 30 nM Factor XI in Factor XI deficient plasma. The following fucoidans were tested: *Ascophyllum nodosum*, high MW, 10 nM; *Fucus vesiculosus*, 100 nM; *Undaria pinnatifida*, 100 nM; *Ascophyllum nodosum*, low MW, 1000 nM. Results are shown in Table 16 below.

TABLE 16

| | +30 nM Factor XI | | No added Factor XI | |
|---|---|---|---|---|
| Compound | Peak time (min) | Peak thrombin (nM) | Peak time (min) | Peak thrombin (nM) |
| A. n. LMW | 28.8 | 67.9 | 46.5 | 2.9 |
| F. v. | 29.8 | 70.8 | 44.5 | 2.4 |
| U. p. | 26.3 | 116.6 | 42.5 | 2.5 |
| A. n. HMW | 26.0 | 86.8 | 48.3 | 2.3 |
| None | 51.7 | 36.0 | >120 | 0.2 |

Results show that all fucoidans stimulated thrombin generation in FXI deficient plasma supplemented with Factor XI. In the absence of added Factor XI, no thrombin peaks were generated by fucoidan. These results verify the Factor XI-dependency of the stimulation of thrombin generation by fucoidans.

Example 12

Fucoidans Act by Activating FXI

The FXI-dependent mechanism of fucoidan stimulation of thrombin generation was studied in a CAT assay in which activated FXI (FXIa) was added to FXI deficient plasma. No tissue factor was added. The following fucoidans were tested: *Ascophyllum nodosum*, high MW, 10 nM; *Fucus vesiculosus*, 100 nM; *Undaria pinnatifida*, 100 nM; *Ascophyllum nodosum*, low MW, 1000 nM.

A thrombin peak was observed in FXI deficient plasma to which 60 pM human plasma FXIa (Enzyme Research Laboratories, South Bend, Ill., USA) was added. However, the addition of fucoidans to the FXI deficient plasma+FXIa did not increase peak thrombin or decrease peak time. From this experiment, it appears that the fucoidans normally act to activate or enhance the activation of FXI to FXIa. When FXIa is provided, the fucoidans had no further stimulatory effect.

Example 13

Fucoidans Stimulate Thrombin Generation in Extrinsically Compromised Plasma

The effect of fucoidan stimulation of thrombin generation was studied in FVII deficient plasma at a range of concentrations of tissue factor. As FVII is the first coagulation factor in the extrinsic pathway, FVII deficient plasma is extrinsically compromised. In the absence of fucoidan, there was only a small thrombin peak which had a large peak time at high tissue factor concentration (20 pM). The thrombin peak may have been caused by residual FVII. Tissue factor concentrations lower than 5 pM gave no thrombin generation. When 100 nM *Undaria pinnatifida* fucoidan was included, a large thrombin peak was obtained. Increasing the concentration of tissue factor had little effect on peak thrombin, and reduced peak time only slightly. Results are shown in Table 17 below.

TABLE 17

| | Peak thrombin (nM) | Peak time (min) | Peak thrombin (nM) | Peak time (min) | Peak thrombin (nM) | Peak time (min) | Peak thrombin (nM) | Peak time (min) |
|---|---|---|---|---|---|---|---|---|
| | | | | Tissue factor (pM) | | | | |
| | 0 | | 1 | | 5 | | 20 | |
| +fucoidan | 303.1 | 15.8 | 305.9 | 14.0 | 313.4 | 12.5 | 285.3 | 11.7 |
| −fucoidan | 0 | >120 | 0 | >120 | 0 | >120 | 27.6 | 51.0 |

The results show that when the extrinsic pathway is prevented from acting by the absence of FVII, tissue factor has little effect on the stimulation of thrombin generation by fucoidan.

In a further experiment, fucoidan stimulation of thrombin generation was studied in FVII deficient plasma or FVIII inhibited FVII deficient plasma at a range of tissue factor concentrations. Thrombin peaks stimulated by 100 nM *Undaria pinnatifida* fucoidan in the FVIII inhibited FVII deficient plasma were small and delayed, even in the presence of high tissue factor concentrations, compared to the peaks stimulated in the FVII deficient plasma. Results are shown in Table 18 below.

TABLE 18

| | Tissue factor (pM) | | | | | | | |
|---|---|---|---|---|---|---|---|---|
| | 0 | | 1 | | 5 | | 20 | |
| Plasma | Peak thrombin (nM) | Peak time (min) | Peak thrombin (nM) | Peak time (min) | Peak thrombin (nM) | Peak time (min) | Peak thrombin (nM) | Peak time (min) |
| FVII deficient | 303.1 | 15.8 | 305.9 | 14.0 | 313.4 | 12.5 | 285.3 | 11.7 |
| FVIII inhibited FVII deficient | 0 | >120 | 2.6 | 38.3 | 15.4 | 32.2 | 62.7 | 26.8 |

The results show that in extrinsically compromised plasma, fucoidan acts to stimulate thrombin generation via the intrinsic pathway, even at high tissue factor concentrations.

Example 14

Sulfated Polysaccharides may be Useful in Place of Coagulation Factor Therapy in Hemophilia Patients with less than 1% normal FVIII are considered to have severe hemophilia, with 1-5% moderately severe hemophilia, and with more than 5% but less than 40% mild hemophilia. An experiment was performed to evaluate fucoidan stimulated thrombin generation at low concentrations of FVIII that reflect the levels of FVIII present in plasma of patients with hemophilia A. No tissue factor was added. Fucoidans from *Undaria pinnatifida* (100 nM) and *Ascophyllum nodosum*, high MW (10 nM) were tested. FVIII was added to FVIII deficient plasma at a range of concentrations to provide FVIII at 0, 0.2, 0.5, 1, 2 or 10% of the FVIII present in normal plasma. These figures do not take into account any residual FVIII present in the FVIII deficient plasma. Results are shown in Table 19 below. In a control experiment, the plasma was pre-incubated with anti-FXI antibody. No thrombin peaks were observed in the presence of either fucoidan at any of the concentrations of FVIII tested (not shown).

TABLE 19

| | % FVIII compared to normal plasma | | | | | |
|---|---|---|---|---|---|---|
| fucoidan | 0 | 0.2 | 0.5 | 1 | 2 | 10 |
| | Peak thrombin (nM) | | | | | |
| *U. pinnatifida* | 5.6 | 35.0 | 54.1 | 65.9 | 74.7 | 93.3 |
| *A. nodosum* | 0 | 2.4 | 6.4 | 10.2 | 19.3 | 35.8 |
| — | 0 | 0 | 0 | 0 | 0 | 0 |

TABLE 19-continued

| | % FVIII compared to normal plasma | | | | | |
|---|---|---|---|---|---|---|
| fucoidan | 0 | 0.2 | 0.5 | 1 | 2 | 10 |
| | Peak time (min) | | | | | |
| *U. pinnatifida* | 50.2 | 42.7 | 38.3 | 34.2 | 33.0 | 28.3 |
| *A. nodosum* | >120 | 56.9 | 51.4 | 46.5 | 42.3 | 34.2 |
| — | >120 | >120 | >120 | >120 | >120 | >120 |

Results show that even at low concentrations of FVIII, sulfated polysaccharides stimulate thrombin generation. The absence of any thrombin peaks when FXI is inhibited show that a FXI dependent mechanism is responsible for this activity. Thus, sulfated polysaccharides may be useful in treating hemophiliacs via a FXI-dependent mechanism.

Example 15

Sulfated Polysaccharides may be Useful in Place of Coagulation Factor Therapy in Hemophilia B Sulfated polysaccharides were tested at a range of concentrations in hemophilia B plasma in the CAT assay. The concentration of tissue factor was 1 pM. At concentrations of up to 100 nM, fucoidan from *Fucus vesiculosus* improved thrombin generation parameters (i.e. increased peak thrombin and decreased peak time) in a concentration-dependent manner. At higher fucoidan concentrations of 250, 800 and 2000 nM, thrombin generation parameters deteriorated in a concentration-dependent manner. A similar pattern was observed for each of the sulfated polysaccharides tested, with an optimal effect on thrombin generation at an intermediate concentration, and sub-optimal effects at lower and higher concentrations. The optimal effect was achieved at a comparable μg/ml concentration of each sulfated polysaccharide, although the nM concentrations varied over two orders of magnitude. The FIX equivalent activity of the concentration of each of the six sulfated polysaccharides tested that had the most beneficial effect on peak thrombin was estimated. Results are shown in Table 20 below.

TABLE 20

| Sulfated polysaccharide | Conc (nM) | Conc (μg/ml) | FIX EA (mU/ml) |
| --- | --- | --- | --- |
| PPS | 1000 | 5.9 | 32 |
| Fuc An LMW | 1000 | 7.5 | 58 |
| Fuc Fv | 100 | 11.6 | 42 |
| Fuc Up | 100 | 12.7 | 41 |
| Fuc An HMW | 25 | 15.0 | 80 |
| Fuc Lj | 10 | 10.0 | 76 |

Further data are given in Table 21 below, indicating the "therapeutic window" for each sulfated polysaccharide. The "therapeutic window" is the concentration range at which the sulfated polysaccharide provides for a peak thrombin in severe hemophilia B plasma (FIX activity below 1% of normal plasma) which is at least the peak thrombin provided by the addition of 10 mU/mL (1%) of factor IX to severe hemophilia B plasma. Also shown is the FIX equivalent activity of the optimal concentration of sulfated polysaccharide and, in brackets, the FIX equivalent activity of the polysaccharide concentration at either end of the therapeutic window. The results indicate that each sulfated polysaccharide has a procoagulant effect across a broad concentration range.

TABLE 21

| Sulfated polysaccharide | MW (kD) | Therapeutic window | | FIX EA (mU/ml) |
| --- | --- | --- | --- | --- |
| | | nM | μg/mL | |
| PPS | 5.9 | 250-6667* | 1.5-39 | 32 (27-12) |
| A. n. LMW | 7.5 | 100-20000* | 0.8-150 | 58 (13-28) |
| F. v. | 115 | 20-2000* | 2.3-232 | 42 (26-12) |
| U. p. | 127 | 8-2000* | 1.0-254 | 41 (11-19) |
| A. n. HMW | 600 | 5-333 | 3-200 | 80 (28-22) |
| L. j. | >1000 | 2.5-100 | 2.5-100 | 76 (22-23) |

*indicates that the upper limit given for the therapeutic window was the highest concentration of sulfated polysaccharide tested.

Example 16

Treatment of a Patient Dependent on Factor XI Status

A patient may consult a physician prior to elective surgery. As the surgery carries the risk of bleeding, the physician may plan to administer a sulfated polysaccharide before or shortly after surgery, in the event that the patient suffers undue bleeding following surgery. The physician will wish to check whether the patient is suitable for such therapy, and will therefore check the patient's records and/or perform testing to determine whether the patient has hemophilia C. Certain patients may be at particular risk of hemophilia C, for example patients having a family history of the condition.

If the patient has a normal level of plasma factor XI:c activity (greater than 70 IU/dL), the patient can be administered a sulfated polysaccharide either before surgery, or following surgery in the event that they suffer bleeding.

If the patient has a partial deficiency (plasma factor XI:c activity of 20-70 IU/dL), or a severe deficiency (plasma factor XI:c activity of less than 20 IU/dL), the physician may decide to administer the sulfated polysaccharide before or after surgery in combination with factor XI concentrate or fresh frozen plasma.

The invention claimed is:

1. A method of identifying a non-anticoagulant sulfated polysaccharide (NASP) which is capable of enhancing blood coagulation in dependence on FXI, the method comprising:
    a) combining a blood or plasma sample comprising activation competent FXI with a composition comprising a sulfated polysaccharide and measuring the clotting or thrombin generation parameters of the blood or plasma sample;
    b) combining a corresponding blood or plasma sample deficient in activation competent FXI with a composition comprising the sulfated polysaccharide and measuring the clotting or thrombin generation parameters of the blood or plasma sample; and
    c) comparing the clotting or thrombin generation parameters of the blood or plasma samples as determined in steps (a) and (b) with each other, wherein a decrease in the clotting time of the blood sample or an increase in peak thrombin or decrease in peak time of the plasma sample comprising activation competent FXI compared to the clotting time of the blood sample or peak thrombin or peak time of the plasma sample deficient in activation competent FXI is indicative of a NASP which is capable of enhancing blood coagulation in dependence on FXI.

2. The method according to claim 1, wherein the NASP is a fucoidan.

3. The method according to claim 2, wherein the fucoidan is a *Fucus vesiculosis* fucoidan.

4. The method according to claim 1, wherein the NASP is present at concentration of from 20 to 2000 nM.

5. The method according to claim 1, wherein the plasma sample comprising activation competent FXI and the plasma sample deficient in activation competent FXI are normal plasmas.

6. The method according to claim 1, wherein the plasma sample comprising activation competent FXI and the plasma deficient in activation competent FXI are Factor XII-deficient plasmas.

7. The method according to claim 1, wherein the plasma sample comprising activation competent FXI and the plasma sample deficient in activation competent FXI further comprise an inhibitor of Factor XII.

8. The method according to claim 7, wherein the inhibitor is corn trypsin inhibitor (CTI).

9. The method according to claim 1, wherein a decrease in the clotting time of the blood sample or an increase in peak thrombin or decrease in peak time of the plasma sample comprising activation competent FXI compared to the clotting time of the blood sample or peak thrombin or peak time of the plasma sample deficient in activation competent FXI indicative that the NASP is an activator of Factor XI.

10. A method of identifying a non-anticoagulant sulfated polysaccharide (NASP) which is capable of enhancing blood coagulation in FXI dependent manner, the method comprising:

a) combining a blood or plasma sample comprising activation competent FXI with a composition comprising a sulfated polysaccharide and measuring the clotting or thrombin generation parameters of the blood or plasma sample;
b) combining a corresponding blood or plasma sample deficient in activation competent FXI with a composition comprising the sulfated polysaccharide and activated Factor XI (FXIa) and measuring the clotting or thrombin generation parameters of the blood or plasma sample; and
c) comparing the clotting or thrombin generation parameters of the blood or plasma samples as determined in steps (a) and (b) with each other, wherein a result of no decrease in the clotting time of the blood sample or no increase in peak thrombin or no decrease in peak time of the plasma sample comprising activation competent FXI compared to the clotting time of the blood sample or peak thrombin or peak time of the plasma sample deficient in activation competent FXI is indicative that the NASP is an activator of Factor XI.

11. The method according to claim 10, wherein the NASP is a fucoidan.

12. The method according to claim 11, wherein the fucoidan is *Fucus vesiculosis* fucoidan.

13. The method according to claim 10, wherein the NASP is present at a concentration of from 20 to 2000 nM.

14. The method according to claim 10, wherein FXIa is present at a concentration of 60 pM.

* * * * *